(12) United States Patent
Dong

(10) Patent No.: US 6,939,372 B2
(45) Date of Patent: *Sep. 6, 2005

(54) LOW PROFILE, HIGH STRETCH, LOW DILATION KNIT PROSTHETIC DEVICE

(75) Inventor: Jerry Q. Dong, Oakland, NJ (US)

(73) Assignee: SciMed Life Systems, Inc., Maple Grove, MN (US)

( * ) Notice: Subject to any disclaimer, the term of this patent is extended or adjusted under 35 U.S.C. 154(b) by 64 days.

This patent is subject to a terminal disclaimer.

(21) Appl. No.: 10/410,482

(22) Filed: Apr. 9, 2003

(65) Prior Publication Data

US 2003/0204241 A1 Oct. 30, 2003

Related U.S. Application Data

(63) Continuation-in-part of application No. 10/323,569, filed on Dec. 19, 2002, which is a continuation of application No. 09/898,103, filed on Jul. 3, 2001, now Pat. No. 6,554,855.

(51) Int. Cl.[7] .............................. A61F 2/06; D04B 1/22
(52) U.S. Cl. .......................... 623/1.13; 623/1.5; 66/195
(58) Field of Search .............................. 623/1.13–1.54; 66/192–195

(56) References Cited

U.S. PATENT DOCUMENTS

| | | | |
|---|---|---|---|
| 3,340,134 A | 9/1967 | Porter et al. | |
| 3,474,644 A | 10/1969 | Frank | |
| 3,986,828 A | 10/1976 | Hoffman, Jr. et al. | |
| 4,015,451 A | 4/1977 | Gajjar | |
| 4,052,866 A | 10/1977 | Saunders | |
| 4,064,712 A | 12/1977 | Sayre et al. | |
| 4,193,137 A | 3/1980 | Heck | |
| 4,307,587 A | 12/1981 | Baesgen et al. | |
| 5,407,722 A | 4/1995 | Peake, III et al. | |
| 5,449,530 A | * 9/1995 | Peake et al. | ................. 427/244 |
| 5,456,711 A | * 10/1995 | Hudson | ....................... 623/1.5 |
| 5,611,127 A | 3/1997 | Ceriani et al. | |
| 5,732,572 A | * 3/1998 | Litton | ......................... 66/195 |
| 5,843,158 A | 12/1998 | Lenker et al. | |
| 6,217,609 B1 | 4/2001 | Haverkost | |
| 6,287,316 B1 | * 9/2001 | Agarwal et al. | ............. 606/151 |
| 6,408,656 B1 | * 6/2002 | Ory et al. | ...................... 66/195 |
| 6,547,820 B1 | * 4/2003 | Staudenmeier | .............. 623/1.49 |
| 6,554,855 B1 | * 4/2003 | Dong | ......................... 623/1.13 |
| 2003/0125796 A1 | * 7/2003 | Dong | ......................... 623/1.13 |

FOREIGN PATENT DOCUMENTS

| | | |
|---|---|---|
| EP | 0 464 755 | 1/1992 |
| EP | 0 656 196 | 6/1995 |
| FR | 2 714 816 A1 | 4/2001 |
| WO | WO 00/78250 | 12/2000 |

* cited by examiner

*Primary Examiner*—David H. Willse
*Assistant Examiner*—Suzete J. Gherbi
(74) *Attorney, Agent, or Firm*—Hoffmann & Baron, LLP

(57) ABSTRACT

A radially expandable stent-graft endoprosthesis includes a knitted tubular structure circumferentially disposed and securably attached to the stent. The knitted tubular structure has a warp knit pattern of interlacing yarns with at least a two-needle underlap to provide greater than 50 percent longitudinal stretchability while substantially inhibiting dilation. A knitted tubular graft is combined with an ePTFE liner to form a composite with greater than 50 percent longitudinal stretchability is also provided. The knitted tubular graft also has a warp knit pattern of interlacing yarns with at least a two-needle underlap to provide the longitudinal stretchability while also substantially inhibiting dilation.

42 Claims, 14 Drawing Sheets

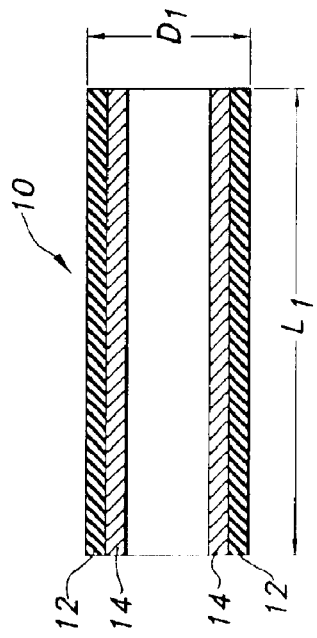
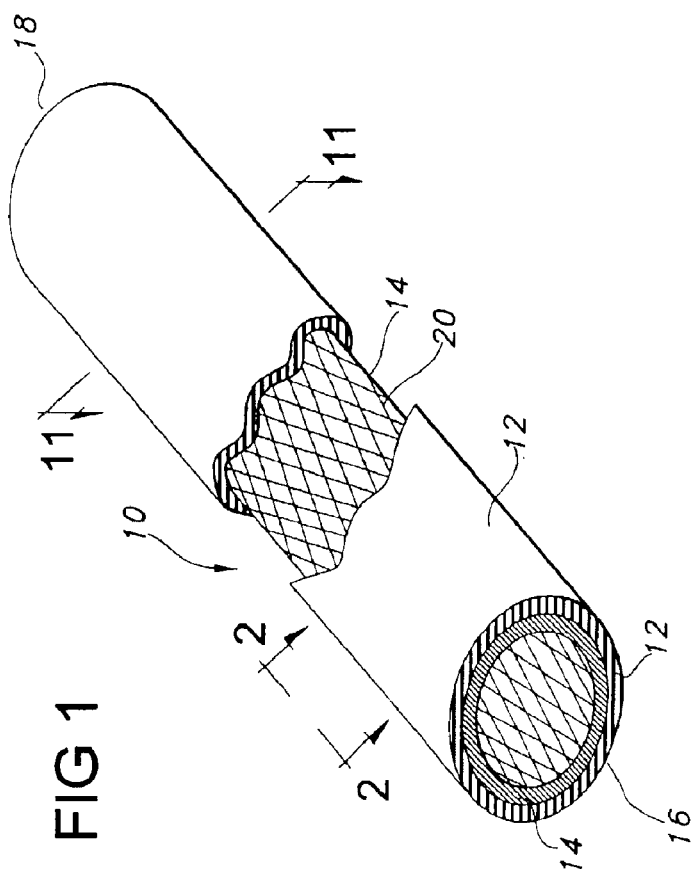
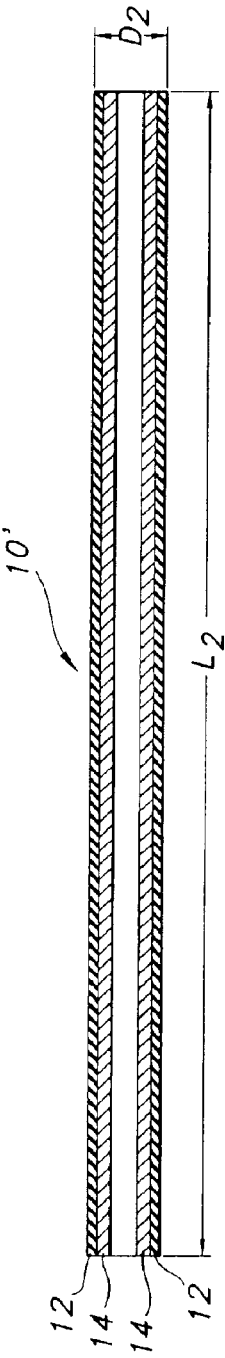

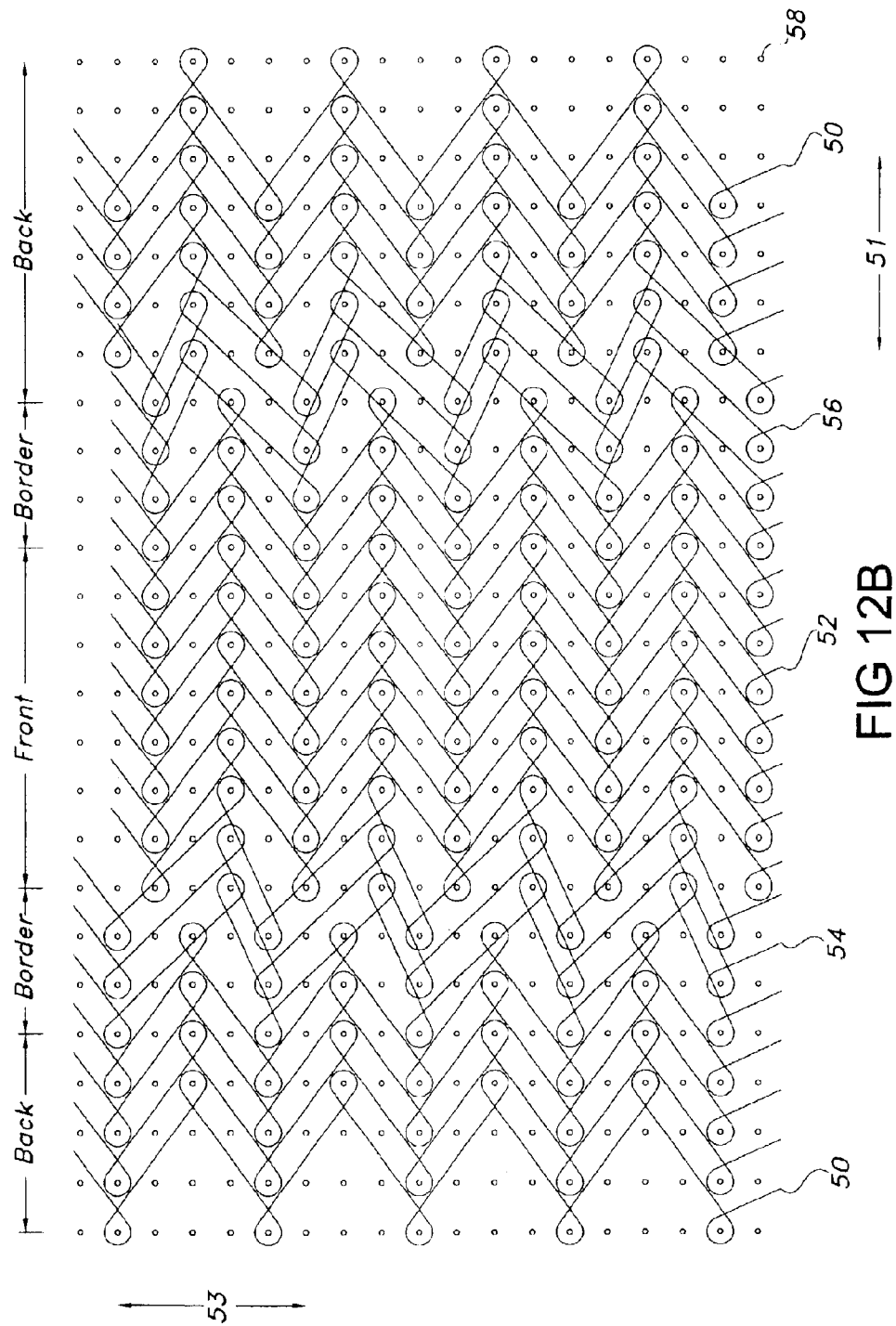

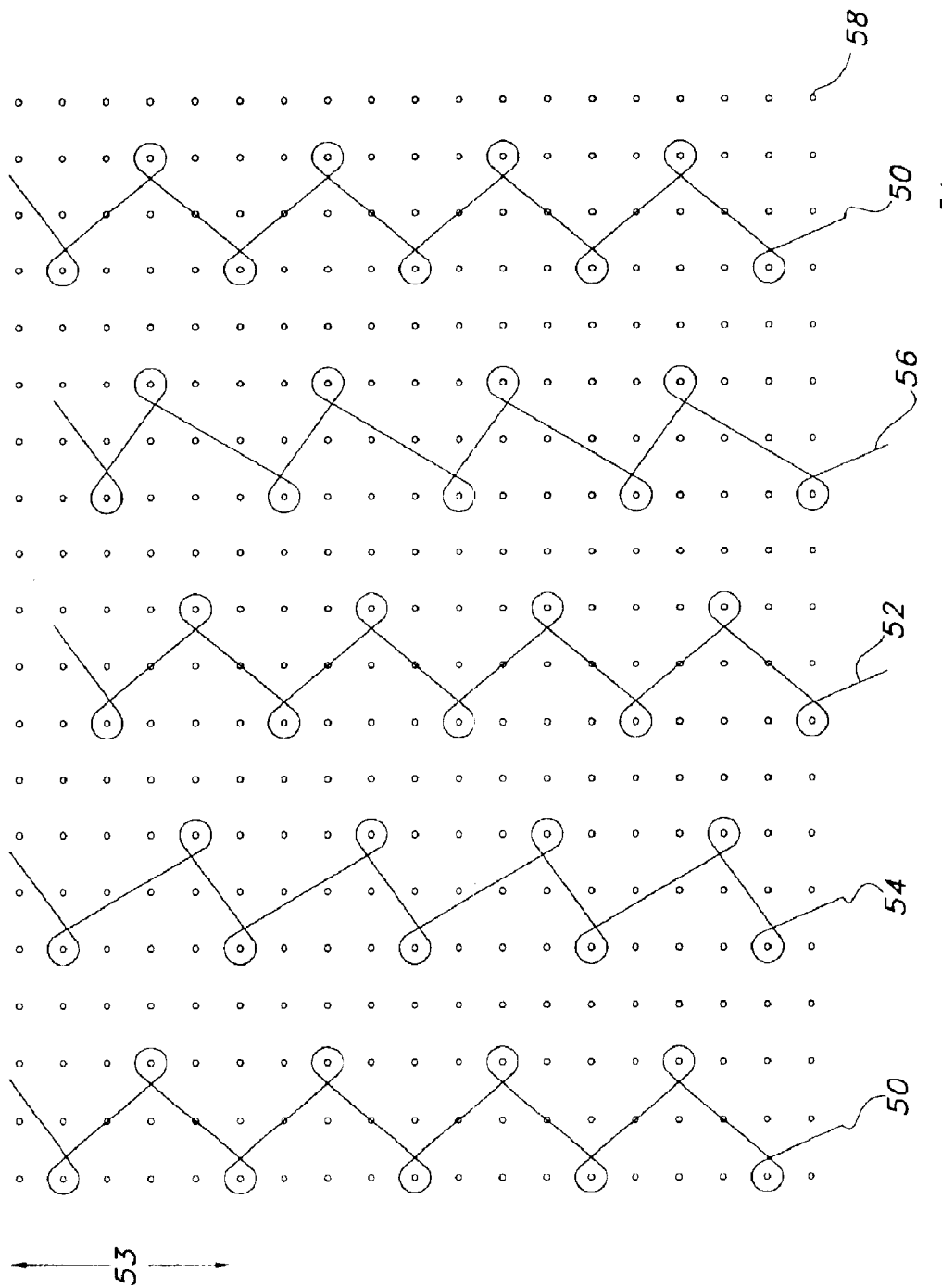

LOW PROFILE, HIGH STRETCH, LOW DILATION KNIT PROSTHETIC DEVICE

CROSS-REFERENCE TO RELATED APPLICATION

The present application is a continuation-in-part of U.S. patent application Ser. No. 10/323,569, filed Dec. 19, 2002, which is a continuation of U.S. patent application Ser. No. 09/898,103, filed Jul. 3, 2001 now U.S. Pat. No. 6,554,855, the contents of which is incorporated herein by reference.

FIELD OF INVENTION

The present invention relates generally to a tubular implantable prosthesis having a knitted textile structure. More particularly, the present invention relates to an endoprosthesis with a knitted textile structure having increased longitudinal stretchability and further having radially restricted enlargement.

BACKGROUND OF RELATED TECHNOLOGY

An intraluminal prosthesis is a medical device used in the treatment of diseased blood vessels. An intraluminal prosthesis is typically used to repair, replace, or otherwise correct a diseased or damaged blood vessel. An artery or vein may be diseased in a variety of different ways. The prosthesis may therefore be used to prevent or treat a wide variety of defects such as stenosis of the vessel, thrombosis, occlusion or an aneurysm.

One type of intraluminal prosthesis used in the repair of diseases in various body vessels is a stent. A stent is a generally longitudinal tubular device formed of biocompatible material which is useful to open and support various lumens in the body. For example, stents may be used in the vascular system, urogenital tract and bile duct, as well as in a variety of other applications in the body. Endovascular stents have become widely used for the treatment of stenosis, strictures and aneurysms in various blood vessels. These devices are implanted within the vessel to open and/or reinforce collapsing or partially occluded sections of the vessel.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Structures which have been used as intraluminal vascular grafts have included coiled stainless steel springs; helically wound coil springs manufactured from a heat-sensitive material; and expanding stainless steel stents formed of stainless steel wire in a zig-zag pattern. Examples of various stent configurations are shown in U.S. Pat. No. 4,503,569 to Dotter; U.S. Pat. No. 4,733,665 to Palmaz; U.S. Pat. No. 4,856,561 to Hillstead; U.S. Pat. No. 4,580,568 to Gianturco; U.S. Pat. No. 4,732,152 to Wallsten and U.S. Pat. No. 4,886,062 to Wiktor, all of whose contents are incorporated herein by reference.

A graft is another commonly known type of intraluminal prosthesis which is used to repair and replace various body vessels. A graft provides a lumen through which blood may flow. Moreover, a graft is often configured to have porosity to permit the ingrowth of cells for stabilization of an implanted graft while also being generally impermeable to blood to inhibit substantial leakage of blood therethrough. Grafts are typically tubular devices which may be formed of a variety of materials, including textile and non-textile materials.

A stent and a graft may be combined into a stent-graft endoprosthesis to combine the features thereof. The graft, however, in the stent-graft endoprosthesis should comply with the implantation requirements of the stent which often include collapsing the stent for placement at an implantation site and expansion of the stent for securement thereat. Grafts which cannot easily accommodate the longitudinal and/or radial dimensional changes from an unexpanded or collapsed state to an expanded stent often complicate the implantation of the stent-graft. For instance, some grafts are folded in the collapsed or unexpanded state and must be subsequently be unfolded to accommodate the expanded stent. The unfolding of the graft, however, often complicates the placement of the graft on the stent and the implantation of the stent-graft itself. Alternatively, noncontiguous grafts have been used with expandable stent-grafts. Upon expansion of the stent, however, portions of the noncontiguous graft often separate to accommodate the stent expansion. This separation leaves gaps in the graft structure thereby permitting the leakage of blood through these gaps.

Moreover, an intraluminal device, such as a stent, a graft or a stent-graft, may dilate over time after implantation within a bodily lumen. The dilation of the implanted intraluminal device is a radial enlargement of the device resulting from pulsating stresses or pressures present within the bodily lumen. The actions of the pulsating stresses or pressures often fatigue the structure of the device resulting in radial expansion and possibly longitudinal foreshortening.

A variety of mechanical means have been used to attempt to limit device dilation. For example, U.S. Pat. No. 5,843,158 to Lenker et al. describes the use of generally inelastic frame rings circumferentially disposed along a radially contractible stent-graft. The frames are described as limiting the radial expansion. Such frames, however, must be integral to the stent and complicate the stent-graft geometry.

U.S. Pat. No. 5,843,158 to Lenker et al. further describes mechanical means for limiting radial expansion of a graft in a stent-graft. In one alternative, the stent graft includes an internal liner. The internal liner is described as an inelastic material and is folded within the stent graft. Upon radial expansion of stent-graft, the internal liner is described as further limiting the radial expansion of the stent-graft. Furthermore, a graft containing circumferential composite yarns is described as yet another alternative for limiting radial expansion. The composite yarns are described as having inexpansible yarns counter wound or braided over an elastic core yarn. The inexpansive yarns are described as limiting radial expansion of graft. These attempts to limit radial expansion of a stent-graft, however, result in complicated the stent-graft designs that have either additional liners or complex composite yarn designs.

Thus, there is a need for a graft that compliments the implantation of an expandable stent of a stent-graft endoprosthesis and limits dilation without the disadvantages of the prior art. In particular, there is need for a graft that is securably attached to the stent in both the expanded and unexpanded state which limits without complicating the mechanical dynamics of the stent or the graft.

SUMMARY OF THE INVENTION

The present invention provides an implantable tubular prosthesis having a radially expandable tubular stent structure having a first diameter and capable of longitudinal expansion or contraction to achieve a second diameter which is different from the first diameter and a tubular knitted tubular graft circumferentially disposed and securably attached to the stent. The graft has a pattern of interlaced wale and course yarns in a warp knit pattern to permit longitudinal expansion or contraction of the graft substantially consistent with the longitudinal expansion or contraction of the stent.

The prosthesis of the present invention is capable of longitudinal expansion from 50 to 200 percent by length from a quiescent state. Alternatively, the prosthesis of the present invention is capable of 50 to 220 percent longitudinal contraction by length to achieve a substantially quiescent state from an unexpanded state. Furthermore, the textile graft of the present invention is substantially fluid-tight in its quiescent state.

To achieve such a degree of longitudinal expansion or contraction the textile graft includes a single layer, warp knit pattern having a set yarns diagonally shifted over two or more yarns before forming a loop between engaging yarns. The knit pattern is generally described as a warp knit pattern with at least a two needle underlap. Such patterns depart a high degree of flexibility and stretchability to the textile graft of the present invention. Moreover, such patterns substantially inhibit radial expansion of the textile graft beyond a desired diameter to limit dilation of the graft.

In one aspect of the present invention, an implantable tubular prosthesis is provided which is capable of longitudinal expansion from a quiescent state to an elongated state including a radially contractible and longitudinally expandable tubular stent having a quiescent diameter and quiescent length capable of longitudinal expansion to the elongated state having an elongated length and a contracted diameter, wherein the elongated length is greater than the quiescent length and the contracted diameter is smaller than the quiescent diameter, and further wherein the stent is capable of resiliently returning from the elongated state to the quiescent state; and a knitted tubular graft circumferentially disposed and securably attached to the stent in the quiescent state. The graft has a single layer of yarns to define a single layered wall interlaced into stitches in a knit pattern capable of resilient longitudinal elongation and resilient radial contraction of the graft to the elongated state. The graft has from about 400 to about 1,200 stitches per square centimeter to provide compliancy in the quiescent state. The knit pattern is a warp knitted pattern of yarns forming a textile layer having an interior surface and an exterior surface, wherein exterior yarns comprise the exterior surface and form loops in the longitudinal direction of the prosthesis, and interior yarns comprise the interior surface and are diagonally shifted over two or more of the exterior yarns in an alternating pattern along a width of the prosthesis before engaging an exterior yarn.

In another aspect of the present invention, the implantable tubular prosthesis includes a radially contractible and longitudinally expandable tubular stent; a non-textile tubular member circumferentially disposed and securably attached to the interior surface of the stent; and a knitted tubular graft circumferentially disposed to the exterior surface of said stent and securably attached to said non-textile tubular member. The graft has a single layer of yarns to define a single layered graft wall. The yarns are interlaced into stitches in a knit pattern capable of resilient longitudinal elongation and resilient radial contraction of the graft to the elongated state. The graft has greater than about 350 stitches per square centimeter to provide compliancy in the quiescent state. The knit pattern is a warp knitted pattern of yarns forming a textile layer having an interior surface and an exterior surface, wherein exterior yarns comprise the exterior surface and form loops in the longitudinal direction of said prosthesis, and interior yarns comprise the interior surface and are diagonally shifted over two or more of the exterior yarns in an alternating pattern along a width of said prosthesis before engaging an exterior yarn. The interior yarns also inhibit radial expansion of the interior yarns to inhibit dilation of the prosthesis.

In still another aspect of the present invention, an implantable tubular graft is provided which includes a knitted tubular graft having a single layer of yarns to define a single layered wall having an interior surface and an exterior surface and a non-textile tubular member circumferentially disposed and securably attached to the interior surface of the knitted tubular graft. The yarns are interlaced into stitches in a knit pattern capable of resilient longitudinal elongation and resilient radial contraction of the graft to the elongated state and having at least about 350 stitches per square centimeter to provide compliancy in the quiescent state. The knit pattern is a warp knitted pattern of yarns forming a textile layer having an interior surface and an exterior surface, wherein exterior yarns comprise the exterior surface and form loops in the longitudinal direction of the graft, and interior yarns comprise the interior surface and are diagonally shifted over two or more of the exterior yarns in an alternating pattern along a width of the graft before engaging an the exterior yarn.

BRIEF DESCRIPTION OF THE DRAWINGS

FIG. 1 is a partial cut-away perspective view of an endoprosthesis of the present invention having a stent and a graft both capable of longitudinal expansion or contraction.

FIG. 2 is a cross-sectional view of the stent-graft of FIG. 1 taken along the 2—2 axis.

FIG. 3 depicts the stent-graft of FIG. 2 having a longitudinally expanded length.

FIGS. 12A and 13A depict two-needle underlap yarn patterns for the textile portion of FIG. 11A.

FIGS. 12B and 13B depict three-needle underlap yarn patterns for the textile portion of FIG. 11B.

DETAILED DESCRIPTION OF THE INVENTION

Figure 4:
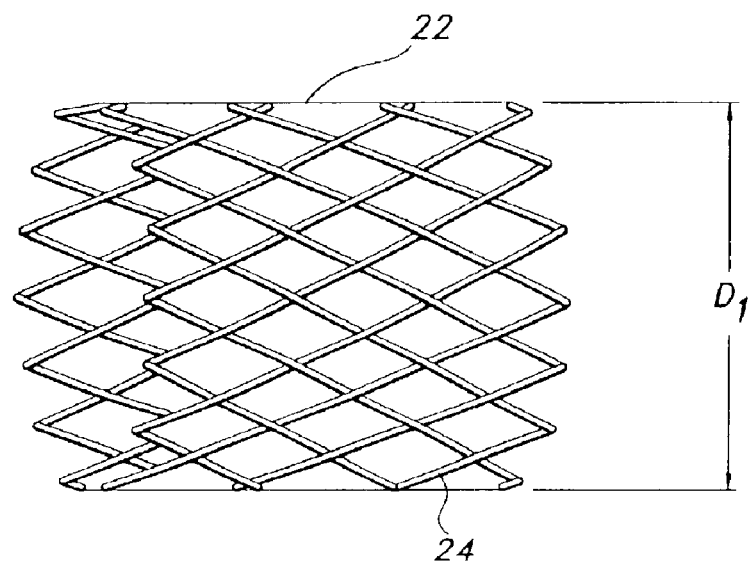
FIG. 4 depicts a wire stent in an expanded state according to the present invention.

The present invention addresses the problems associated with prior art stent-graph endoprosthesis. The stent-graft endoprosthesis of the present invention overcomes the disadvantages of presently available stent-grafts by providing an expandable graft that complements an expandable stent in both an expanded or contracted state and that further substantially inhibits dilation of the stent-graft after implantation into a bodily lumen. Furthermore, the graft of the present invention is knitted textile graft which provides a constraint against undesirable radial expansion while also providing greater longitudinal stretchability than previously knitted or woven textile grafts. Moreover, the knitted textile graft of the present invention has a porosity to permit the ingrowth of cells for the stabilization of implanted endoprosthesis while also being generally impermeable to inhibit substantial leakage of blood therethrough.

FIG. 1 is a depiction of stent-graft 10 of the present invention. Stent-graft 10 is shown as a generally tubular structure with open ends 16, 18 to permit the passage of a bodily fluid therethrough. Stent-graft 10 includes textile graft 12 and stent 14. Textile graft 12 extends circumferentially about stent 14. Textile graft 12 is securably attached to stent 14. The attachment of textile graft 12 to stent 14 may be accomplished by mechanically securing or bonding the textile graft 12 and the stent 14 to one and the other. Mechanical securement includes, but is not limited to, the use of sutures, anchoring barbs, textile cuffs and the like. Bonding includes, but is not limited to, chemical bonding, for instance adhesive bonding, thermal bonding or welding, ultrasonic bonding or welding, and the like.

As depicted in FIG. 1, the textile graft 12 circumferentially extends about an outer stent surface 20. The present invention, however, is not so limited and other stent-graft configurations may suitably be used with the present invention. For instance, textile graft 12 may be circumferentially positioned along an inner surface of stent 14. Moreover, the longitudinal lengths of the stent 14 and the textile graft 12 are not limited to substantially similar lengths as depicted in FIG. 1. For instance, textile graft 12 may be shorter than stent 14 thereby leaving a portion of stent 14 without being covered by textile graft 12.

FIG. 2 dimensionally depicts the stent-graft 10 of the present invention after securement within a bodily lumen (not shown) and FIG. 3 dimensionally depicts the stent-graft 10' prior to securement thereat. To navigate the stent-graft within a bodily lumen the nominal diameter, $D_2$, of stent-graft 10' is smaller than the diameter, $D_1$, of stent-graft 10. Correspondingly, the length, $L_2$, of stent-graft 10' is larger than the length, $L_1$, of stent-graft 10. The textile graft 12 and the stent 14 both conform to these general dimensional depictions for the navigation and securement of stent-graft 10 within a bodily lumen. The textile graft 12 is elongated or stretched to accommodate the elongated stent-graft 10'. Correspondingly, textile graft 12 is in a substantially quiescent state to accommodate the stent-graft 10 of FIG. 2. Moreover, textile graft 12 is designed not to radially expand to a diameter substantially greater than the diameter D1 of stent-graft 10. Such a design substantially inhibits dilation of stent-graft 10.

Various stent types and stent constructions may be employed in the invention. Useful stents include, without limitation, self-expanding stents and balloon expandable stents. The stents may be capable of radially contracting or expanding, as well, and in this sense can be best described as radially or circumferentially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents.

The configuration of stent 14 may be of any suitable geometry. As shown in FIG. 4, wire stent 22 is a hollow tubular structure formed from wire strand 24 being arranged in what can be described as a "Z" or a "zig-zag" pattern. Wire strand 24 may be formed by, for example, braiding or spinning it over a mandrel. Alternatively, wire stent 24 may be formed from more than one wire strand.

Figure 5:
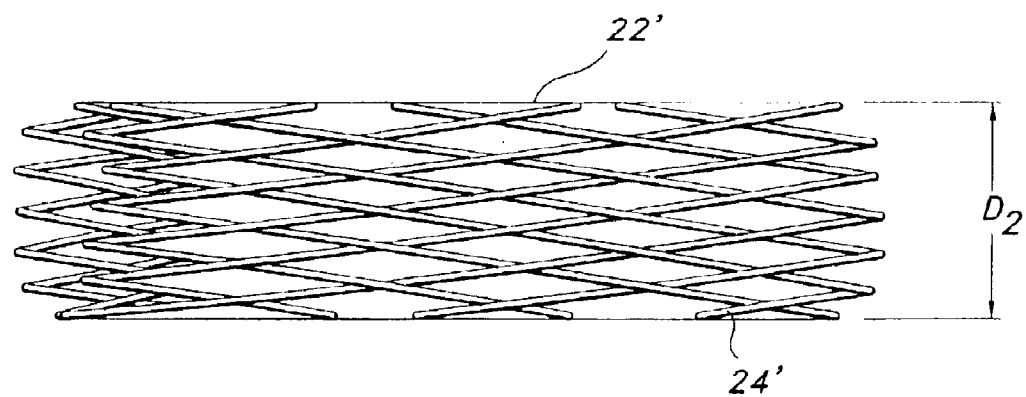
FIG. 5 depicts the wire stent of FIG. 5 in an unexpanded state.

Wire stent 22 is capable of being radially compressed and longitudinally extended, to yield wire stent 22', as depicted in FIG. 5, for implantation into a bodily lumen. The degree of elongation depends upon the structure and materials of the wire stent 22 and can be quite varied. For example, the length of wire stent 22' is from about 50% to about 200% of the length of wire stent 22. The diameter of wire stent 22' may also be up to several times smaller than the diameter of wire stent 22.

Figure 6:
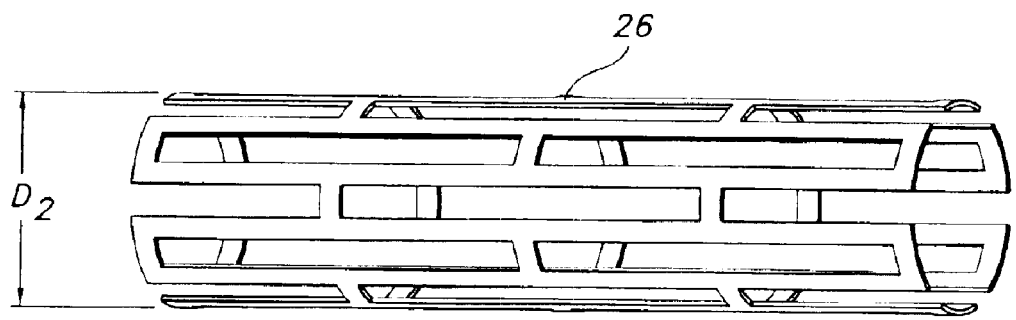
FIG. 6 depicts a slotted stent in a quiescent state according to the present invention.
Figure 7:
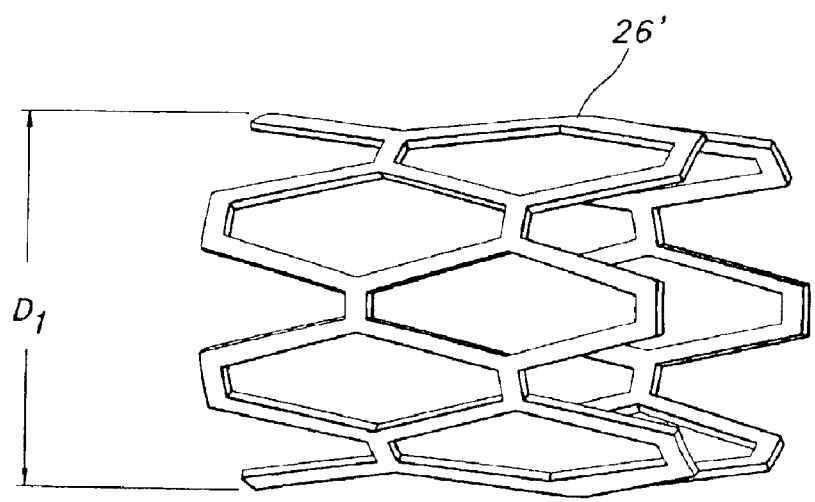
FIG. 7 depicts the slotted-stent of FIG. 6 in an expanded state.

In another aspect of the present invention, a slotted stent 26 is also useful as part of the stent-graft 10. As depicted in FIG. 6, slotted stent 26 is suitably configured for implantation into a bodily lumen (not shown). Upon locating the slotted stent 26 at the desired bodily site, slotted stent 26 is radially expanded and longitudinally contracted for securement at the desired site. The expanded slotted stent 26' is depicted in FIG. 7. Slotted stent 26' is from about 50% to about 200% greater in radial dimension as compared to slotted stent 26.

Figure 8:
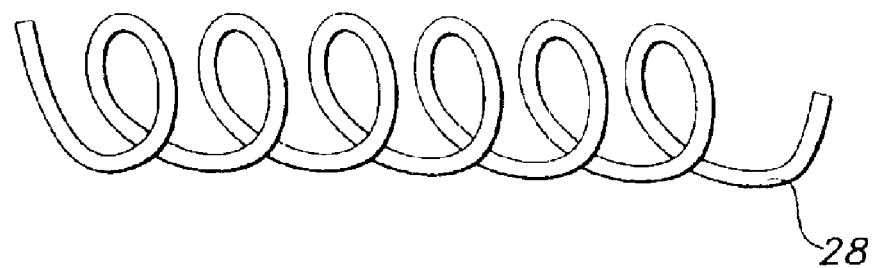
FIG. 8 is a perspective view of a helical coil formed of a single wound wire.
Figure 9:
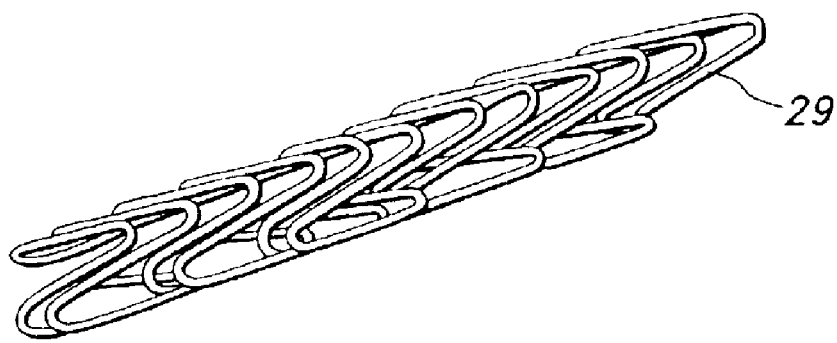
FIG. 9 is a perspective view of a stent having an elongate pre-helically coiled configuration.
Figure 10:
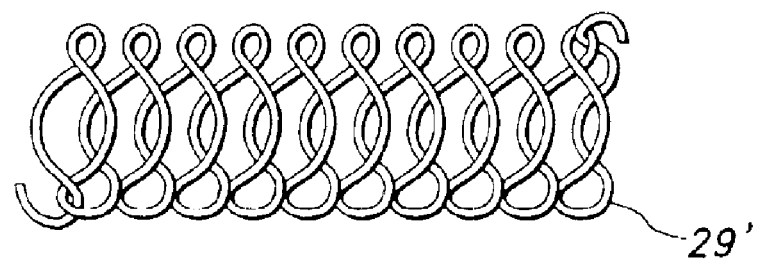
FIG. 10 is a perspective view of the stent of FIG. 9 in a radially expanded state.

Other useful stents capable of radial expansion are depicted in FIGS. 8, 9 and 10. As depicted in FIG. 8, stent 28 is a helical coil which is capable of achieving a radially expanded state (not shown). Stent 29, as depicted in FIG. 9, has an elongate pre-helically coiled configuration as shown by the waves of non-overlapping undulating windings. Stent 29 is capable of being radially expanded to expanded stent 29' as depicted in FIG. 10. These helically coiled or pre-helically stents are also useful with the practice of the present invention.

The textile graft 12 is a knitted textile graft. Knitting involves the interlooping or stitching of yarn into vertical columns (wales) and horizontal rows (courses) of loops to form the knitted fabric structure. Warp knitting is particularly useful with the textile graft 12 of the present invention. In warp knitting, the loops are formed along the textile length, i.e., in the wale or warp direction of the textile. For a tubular textile, such as textile graft 12, stitches in the axial or longitudinal direction of the tubular textile are called wales and stitches in the radial or circumferential direction of the tubular textile are called courses.

Conventional knitted tubular grafts often had to reduce the number of wales per inch to reduce the tendency of a graft to dilate. A low number of wales per inch, however, often reduce compliance of the graft where the graft may not be fluid-tight, i.e., preventing flow of blood therethrough, without other sealing mechanisms. Conventional grafts also used inelastic or a combination of inelastic and elastic yarns to limit radial expansion of a knitted textile graft. The textile graft 12 of the present invention is not so limited. The textile graft 12 uses a novel knit pattern which by itself substantially inhibits undesirable radial expansion. Moreover, the knit pattern of the present invention allows for radial contraction and longitudinal elongation of the textile graft 12 while still providing a constraint to limit radial expansion.

Moreover, conventional knitted tubular grafts often had to reduce or limit the number of courses per inch to obtain a flexible tubular structure, i.e., a structure with longitudinal stretchability. Reducing the number of courses per inch, however, opens the macroporous structure of the textile. A macroporous textile structure is not desirable as a graft because such a structure is not a fluid tight structure, i.e., blood will flow through the graft. Similarly, if the number of wales per inch was too low, the graft would not seal blood flow. If the number of wales per inch was too high, the graft could dilate with time. Thus, conventional grafts were limited by the total number of courses and wales per inch, which is referred to as the number of picks per square inch or the pick size.

For example, U.S. Pat. No. 5,732,572 to Litton describes a textile tubular prosthesis in a warp-knit having an underlap of greater than two needle spaces to limit dilation. The prosthesis, however, is limited to a pick size of 80 to 350 stitches per square centimeter (520 to 2,260 stitches per square inch) to provide a longitudinally stretchable tubular structure. Such a pick size represents about 9 to 19 courses or wales per centimeter (23 to 48 courses or wales per inch). With such a low pick size the prosthesis of this patent is knitted in multiple layers to provide a fluid tight structure while maintaining some degree of stretchability and resistance to dilation. The textile graft 12 of the present invention is not so limited because of the novel knit pattern used to form the graft as compared to more conventional knit patterns, such as tricot, locknit and the like, or even other stretchable knit patterns interlaced with these patterns.

Moreover, grafts are sometimes crimped with creases or folds which tend to reduce kinking when the graft is bent. The kinking also allows for some elongation of the graft, but such a crimped graft would not be generally useful as a stent-graft because of the gaps that would result between the stent and the crimped graft.

The textile graft 12 is configured to have a high degree of stretchability. As used herein, the term stretchability and its variants refer to a textile capable of substantially reversible elongation between a quiescent state and a stretched state. Desirably, the stretchability of the textile graft 12 is substantially compatible with the dimensional changes associated with an expandable stent having both an expanded and an unexpanded or a contracted state as discussed above. Moreover, textile graft 12 is not a crimped graft and does non-bulgingly contract from the elongated state to the quiescent state. The textile graft 12 substantially abuts the stent along both circumferential and longitudinal portions of the stent without separating or bulging from the stent.

Knitting patterns useful in providing desirable limits to radial expansion while maintaining the desired longitudinal stretchability include those knitting patterns that are not highly interlaced, such as patterns that interlace each adjacent back and front yarn. An example of a highly interlaced and commonly known knitted pattern is a Tricot or Jersey pattern. In contrast the knitting pattern of the present invention is not highly interlaced to provide, among other things, the stretchability of the textile graft for use with an expandable stent.

Figure 11A:
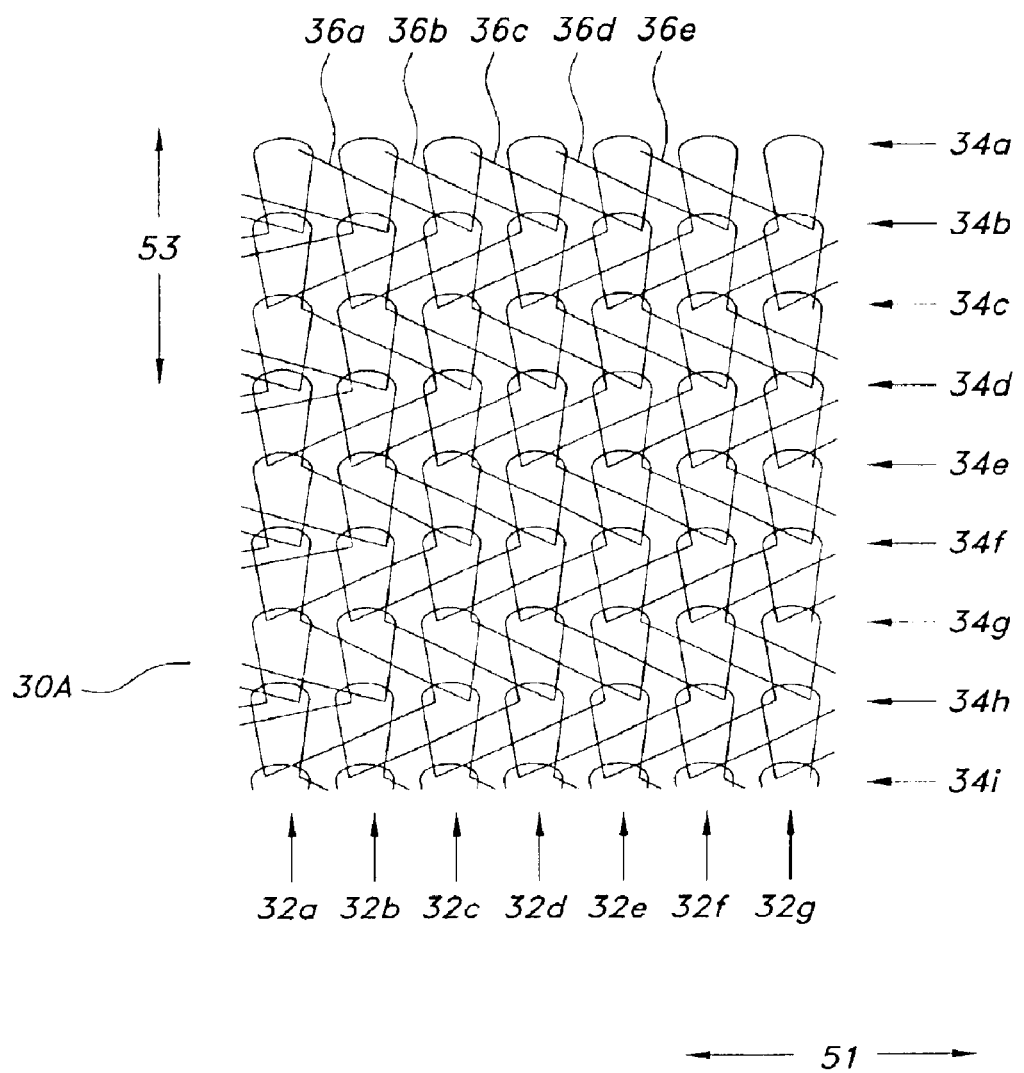
FIG. 11A is an illustration of a textile portion having a two-needle underlap of the graft of FIG. 1 taken along the 11—11 axis.

FIG. 11A is an illustration of portion 30A of textile graft 12 taken along the 11—11 axis. The knitted portion 30A is characterized as a two needle underlap. In FIG. 1A, needle positions in the course direction, i.e., vector 51, are noted by element numbers 32a through 32g and needle positions in the wale direction, i.e., vector 53, are noted by element numbers 34a through 34i. Yarn 36a travels in the course direction from needle position 32a to needle position 32c, or two needle positions, before interlooping with yarn 36c. Yarn 36a then travels two needle positions in the opposite course direction to interloop with a yarn. This alternating two needle position movement is repeated with different yarns to form a knitted pattern with a two needle underlap.

The two needle underlap knitted portion 30A is depicted as a single knitted layer in FIG. 11A, however, the textile graft 12 of the present invention is not so limited. For instance, the knitted portion 30A may include more than one layer of interconnected yarns. In such a multi-layered knitted textile, yarns from one layer are often interlooped with yarns in another layer to form the multi-layered knitted textile.

Textile graft 12 is a flat-knitted tubular structure. To form such a flat-knitted tubular structure, two portions 30A are co-knitted and connected to one and the other joined together by border yarns.

Figure 12A:
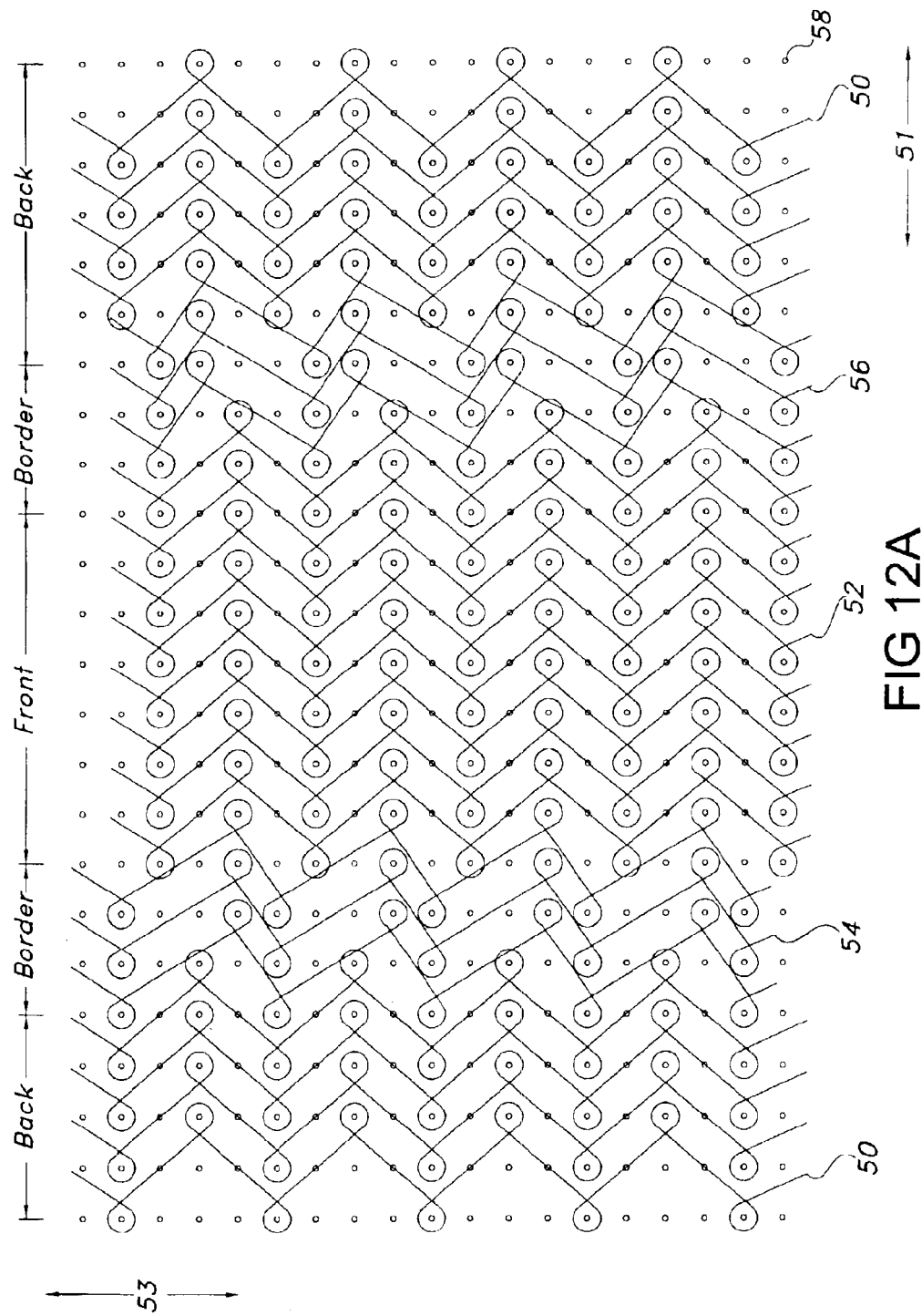

FIG. 12A depicts the two needle underlap yarn patterns of FIG. 11A by separating the front, back and border yarns from one and the other to more clearly illustrate the individual yarn knit pattern and the repeating nature, if any, of these individual yarn knit patterns. As depicted in FIG. 12A, front yarn 52 and back yarn 50 are repeated about 8 times. Border yarns 54 and 56 alternately repeat about three times between the repeating front and back yarn patterns. The front yarn pattern is repeated to yield the technical front or the exterior surface of the textile graft 10 of the present invention. The back yarn pattern is repeated to yield the technical back or the interior surface of the textile graft 10 of the present invention.

The two needle underlap knitting patterns for the front and back yarns are further illustrated in FIG. 13A. The front, back and border yarns are interlaced in a relatively loose pattern having an underlap of at least two needle positions, which are depicted as dots 58. As used herein the term underlap and its variants refer to a yarn that traverses one or more yarns before forming an interlacing loop with a yarn. Such a pattern not only provides stretchability to the textile graft 12 but also provides resistance against dilation. Not wishing to be bound by any particular theory, it is believed that the long underlap in the course direction, which is indicated as vector 51, reduces the potential for expansion in the wale direction, which is indicated by vector 53, because the underlap in the course direction inhibits undesirable radial expansion.

As shown in FIG. 13A, back yarns 50 and front yarns 52 shift diagonally by at least two needle positions in alternating closed-loop interlacing structures. As used herein, closed-loops refer to interlacing yarns where a front or a back yarn crosses over itself in forming the loop. Other patterns useful with the practice of the present invention, such as border patterns, are illustrated in FIG. 13A.

Figure 11B:
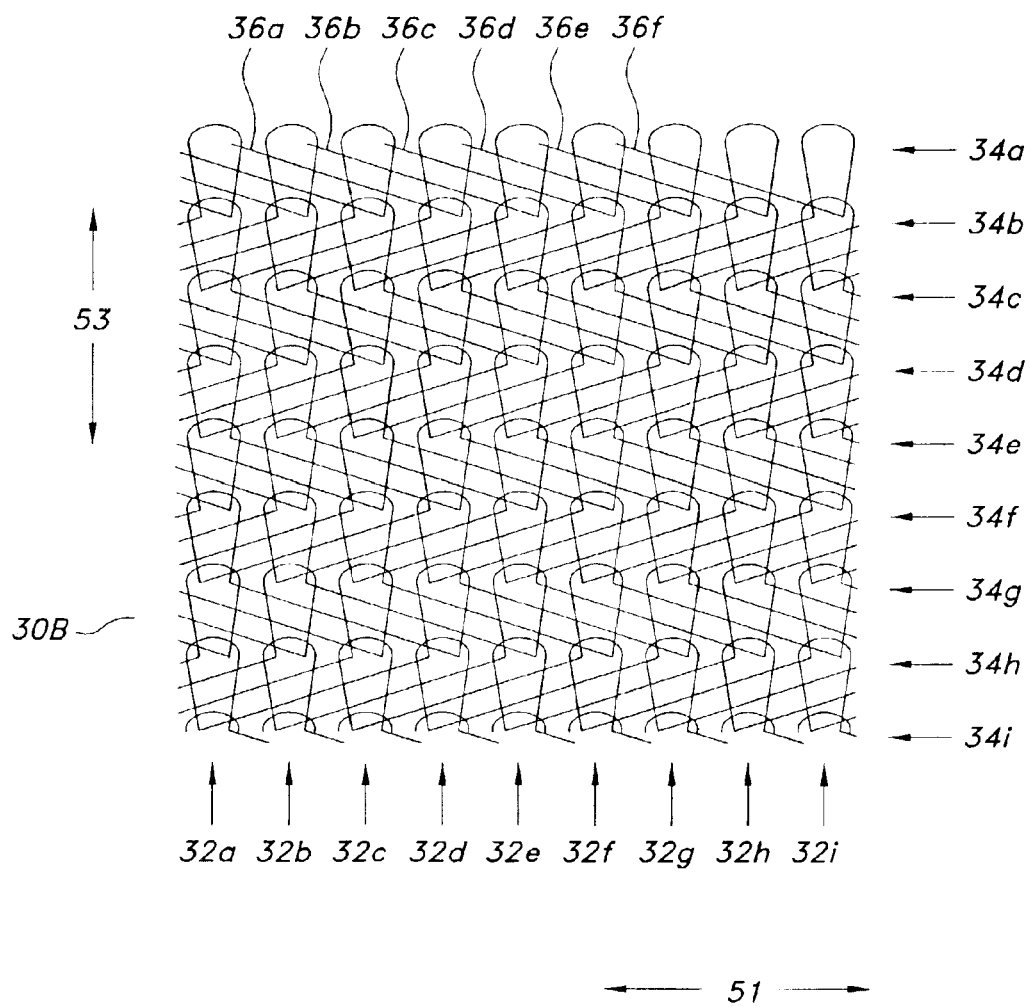
FIG. 11B is an illustration of a textile portion having a three-needle underlap of the graft of FIG. 1 taken along the 11—11 axis.

FIG. 1B is an illustration of portion 30B of textile graft 12 taken along the 11—11 axis. The knitted portion 30B is characterized as a three-needle underlap. In FIG. 11B, needle positions in the course direction, i.e., vector 51, are noted by element numbers 32a through 32i and needle positions in the wale direction, i.e., vector 53, are noted by element numbers 34a through 34i. Yarn 36a travels in the course direction from needle position 32a to needle position 32d, or three needle positions, before interlooping with yard 36d. Yarn 36a then travels three needle positions in t he opposite course direction to interloop with a yarn. This alternating three needle position movement is repeated with different yarns to form a knitted pattern with a three needle underlap.

The knitted portion 30B is depicted as a single knitted layer in FIG. 11B, however, the textile graft 12 of the present invention is not so limited. For instance, the knitted portion 30B may also include more than one layer of interconnected yarns. In such a multi-layered knitted textile, yarns from one layer are often interlooped with yarns in another layer to form the multi-layered knitted textile.

FIG. 12B depicts the three-needle underlap yarn patterns of FIG. 11B by separating the front, back and border yarns from one and the other to more clearly illustrate the individual yarn knit pattern and the repeating nature, if any, of these individual yarn knit patterns. As depicted in FIG. 12B, front yarn 52 and back yarn 50 are repeated about 8 times. Border yarns 54 and 56 alternately repeat about three times between the repeating front and back yarn patterns. The front yarn pattern is repeated to yield the technical front or the exterior surface of the textile graft 10 of the present invention. The back yarn pattern is repeated to yield the technical back or the interior surface of the textile graft 10 of the present invention.

Figure 13B:
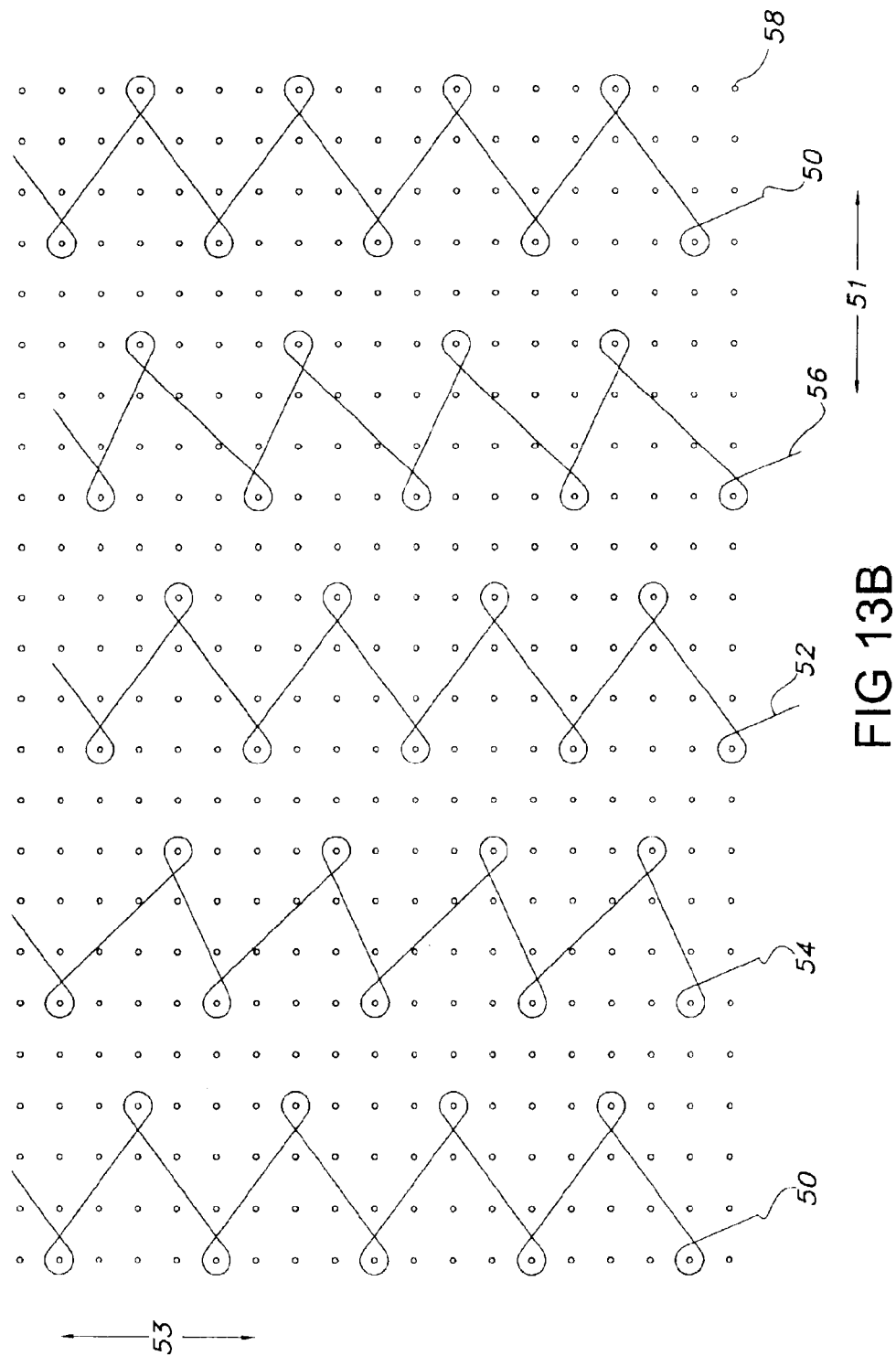

The three-needle underlap knitting patterns for the front and back yarns are further illustrated in FIG. 13B. The front, back and border yarns are interlaced in a relatively loose pattern having an underlap of at least three needle positions, which are depicted as dots 58. As shown in FIG. 13B, back yarns 50 and front yarns 52 shift diagonally by at least three needle positions in alternating closed-loop interlacing structures. Such a pattern not only provides stretchability to the textile graft 12 but also provides resistance against dilation. Not wishing to be bound by any particular theory, it is believed that the long underlap in the course direction, which is indicated as vector 51, reduces the potential for expansion in the wale direction, which is indicated by vector 53, because the underlap in the course direction inhibits undesirable radial expansion.

To knit textile patterns useful with the present invention, double needle bar warp-knitting machine with multiple beams or guide bars is used to form a flat-knitted seamless tubular structure. A typical guide bar layout is shown in Table 1 below. The guide bars are a combination of ground bars and nested connect bars. The threading pattern for each guide bar is shown below in Table 2 for a 72 needle bifurcated (BIF) tube or body and in Table 3 for a 42 needle straight tube (ST) or leg. The arrangement of each needle for the guide bar is shown below in Tables 4 for a first channel, which is used for a body of a bifurcated tube, and in Table 5 for a second channel, which is used for the legs of a bifurcated tube.

TABLE 1

16 Guide Bar Layout:

| 1 | 2 | 3 | 4 | 5 | 6 | 7 | 8 | 9 | 10 | 11 | 12 | 13 | 14 | 15 | 16 |
|---|---|---|---|---|---|---|---|---|----|----|----|----|----|----|----|
| G | G | 3-C-4 | | 5-C-6 | | 7-C-8 | | 9-C-10 | | 11-C-12 | | 13-C-14 | | G | G |

Notes:
G: Ground Bars
C: Nested Connect Bars

TABLE 2

72 Needle Bifurcated (BIF) Tube or Body

| Bar No. | Note: | | ← | | | | (One Repeat Unit) | | | | | | → |
|---|---|---|---|---|---|---|---|---|---|---|---|---|---|
| #16 | not used | | n | n | n | n | n | n | n | n | n | n | n | n |
| #15 | | | n | Y | Y | Y | Y | n | n | Y | Y | Y | Y | n |
| #14 | R | Y | n | n | n | n | n | n | n | n | n | n | n | Y |
| #13 | CL | | n | n | n | n | n | Y | n | n | n | n | n | n |
| #12 | R | | n | n | n | n | n | n | n | n | n | n | Y | n |
| #11 | CR | | n | n | n | n | n | n | Y | n | n | n | n | n |
| #10 | not used | | n | n | n | n | n | n | n | n | n | n | n | n |
| #9 | not used | | n | n | n | n | n | n | n | n | n | n | n | n |
| #8 | not used | | n | n | n | n | n | n | n | n | n | n | n | n |
| #7 | not used | | n | n | n | n | n | n | n | n | n | n | n | n |

TABLE 2-continued

72 Needle Bifurcated (BIF) Tube or Body

| Bar No. | Note: | ← | | | | | (One Repeat Unit) | | | | | → |
|---|---|---|---|---|---|---|---|---|---|---|---|---|
| #6 | CR | n | n | n | n | n | n | Y | n | n | n | n | n |
| #5 | L |   | Y | n | n | n | n | n | n | n | n | n |   |
| #4 | CL | n | n | n | n | n | n | Y | n | n | n | n |   |
| #3 | L | Y | n | n | n | n | n | n | n | n | n | n |   |
| #2 |   | n | n | Y | Y | Y | Y | n | n | Y | Y | Y | Y |
| #1 | not used | n | n | n | n | n | n | n | n | n | n | n |   |

Notes:
L: left body connect
R: right body connect
CL: left leg connect
CR: right leg connect
Bars 4 and 6 join front bar 2
Bars 11 and 13 join back bar 15
Total needles for BIF is 72 * 2 or 144 needles

TABLE 3

42 Needle Straight Tube (ST) or Leg

| Bar No. | Note: | ← | | | (One Repeat Unit) | | | | → |
|---|---|---|---|---|---|---|---|---|---|
| #16 | not used | n | n | n | n | n | n | n | n |
| #15 |   | n | Y | Y | Y | Y | Y | Y | n |
| #14 | R | Y | n | n | n | n | n | n | Y |
| #13 | CL |   | n | n | n | n | n | n | n |
| #12 | R |   | n | n | n | n | n | Y | n |
| #11 | CR |   | n | n | n | n | n | n | n |
| #10 | not used |   | n | n | n | n | n | n | n |
| #9 | not used |   | n | n | n | n | n | n | n |
| #8 | not used |   | n | n | n | n | n | n | n |
| #7 | not used |   | n | n | n | n | n | n | n |
| #6 | CR |   | n | n | n | n | n | n | n |
| #5 | L |   | Y | n | n | n | n | n | n |
| #4 | CL | n | n | n | n | n | n | n | n |
| #3 | L | Y | n | n | n | n | n | n | n |
| #2 |   | n | n | Y | Y | Y | Y | Y | n |
| #1 | not used | n | n | n | n | n | n | n | n |

Notes:
L: left body connect
R: right body connect
CL: left leg connect
CR: right leg connect
Bars 4 and 6 join front bar 2
Bars 11 and 13 join back bar 15
Total needles for ST is (40 for body + 2 for connector) * 2 for total of 84 needles

TABLE 4

Pattern Chains
Top Drum (Body): Channel 1

| Bar #1: | 0-0/0-0// | not used |
| Bar #2: | 0_2-0/4-4/4-6/2-2/ | 2-0/4-4/4-6/2-2_0// |
| Bar #3: | 0_4-2/4-4/2-2/2-0/ | 4-2/4-4/2-2/2-0// |
| Bar #4: | 0_2-0/4-4/4-6/2-2/ | 2-0/4-4/4-6/2-2_0// |
| Bar #5: | 0_2-0/2-2/4-4/4-2/ | 2-0/2-2/4-4/4-2_0// |
| Bar #6: | 0_2-0/4-4/4-6/2-2/ | 2-0/4-4/4-6/2-2_0// |
| Bar #7: | 0-0/0-0// |   |
| Bar #8: | 0-0/0-0// |   |
| Bar #9: | 0-0/0-0// |   |
| Bar #10: | 0-0/0-0// |   |
| Bar #11: | 0_2-2/4-6/2-2/2-0/ | 2-2/4-6/2-2/2-0// |
| Bar #12: | 0_2-2/2-4/0-2/0-0/ | 2-2/2-4/0-2/0-0// |
| Bar #13: | 0_2-2/4-6/2-2/2-0/ | 2-2/4-6/2-2/2-0// |

TABLE 4-continued

Pattern Chains
Top Drum (Body): Channel 1

| Bar #14: | 0-0/0-2/2-4/2-2/ | 0-0/0-2/2-4/2-2_0// |
| Bar #15: | 0_2-2/4-6/2-2/2-0/ | 2-2/4-6/2-2/2-0// |
| Bar #16: | 0-0/0-0// | not used |

TABLE 5

Pattern Chains
Bottom Drum (Legs): Channel 2

| Bar #1: | 0-0/0-0// | not used |
| Bar #2: | 0_2-0/4-4/4-6/2-2/ | 2-0/4-4/4-6/2-2_0// |
| Bar #3: | 0_4-2/4-4/2-2/2-0/ | 4-2/4-4/2-2/2-0// |
| Bar #4: | 0_2-2/4-4/6/2-2/ | 2-2/4-4/6/2-2_0// |
| Bar #5: | 0_2-0/2-2/4-4/4-2/ | 2-0/2-2/4-4/4-2_0// |
| Bar #6: | 0_2-0/2-2/4-4/4-2/ | 2-0/2-2/4-4/4-2_0// |
| Bar #7: | 0-0/0-0// |   |
| Bar #8: | 0-0/0-0// |   |
| Bar #9: | 0-0/0-0// |   |
| Bar #10: | 0-0/0-0// |   |
| Bar #11: | 0_4-2/4-2/2-2/2-0/ | 4-2/4-2/2-2/2-0// |
| Bar #12: | 0_2-2/2-4/0-2/0-0/ | 2-2/2-4/0-2/0-0// |
| Bar #13: | 0_2-2/4-6/2-4/2-2/ | 2-2/4-6/2-4/2-2_0// |
| Bar #14: | 0-0/0-2/2-4/2-2/ | 0-0/0-2/2-4/2-2_0// |
| Bar #15: | 0_2-2/4-6/2-2/2-0/ | 2-2/4-6/2-2/2-0// |
| Bar #16: | 0-0/0-0// | not used |

Figure 20:
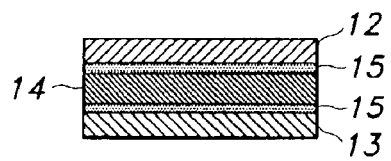
FIG. 20 is a partial cross-section view of the embodiment of FIG. 18 showing a bonding agent for securing the different elements thereat.

In more detail a bifurcated textile graft 120 is depicted in FIG. 20. The bifurcated textile graft 120 has a main body 152 having an open end 146 and having opposed open ends 150 and 148 of leg A 154 and of leg B 156, respectively. Guide bar #2 is utilized for top or front body portion 122. Guide bar #2 is a ground bar and guide bars #2 and #4 join guide bar #2 to make the top or front body portion 122. Guide bar #15 is utilized for bottom or rear body portion 124. Guide bar #15 is also a ground bar and guide bars #11 and #13 join guide bar #15 to make the bottom or rear body portion 124. Guide bars #6 and #13 are utilized for left body portion 128. Guide bars #6 and #11 are utilized for right body portion 126.

Guide bar #2 is utilized for top or front leg portion 130 of leg A154. Guide bar #15 is utilized for bottom or rear leg portion 134 of leg Al 54. Guide bars #6 and #11 are utilized for left leg portion 140 of leg A154. Guide bars #12 and #14 are utilized for right leg portion 142 of leg A154.

Guide bar #2 is also utilized for top or front leg portion 132 of leg B156. Guide bar #15 is also utilized for bottom leg portion 136 of leg B156. Guide bars #3 and #5 are utilized for left leg portion 144 of leg B156. Guide bars #4 and #13 are utilized for right leg portion 138 of leg B156.

The knitted textile graft of the present invention is desirably made on a warp-knitting machine (not shown) using a double needle bar. A useful number of needles per inch for warp knitting is from about 18 to about 36. About 30, or alternatively, about 28 needles per inch are particularly suitable. The trellis of the graft is usually made from a yarn having count from 30 to 300 denier. Desirably, the range of yarn counts for the trellis is from about 30 to about 80. A particularly suitable yarn count is about 40 denier. Moreover, the trellis yarn may be a single ply, a double ply or a multi-ply. The term "multi-ply" is used herein to indicate more than two-ply.

Furthermore, the knitted textile graft of the present invention has greater than 350 stitches per square centimeter, for instance from about 400 to about 1,200 stitches per square centimeter (about 2,600 to about 7,740 stitches per square inch), to provide compliancy of the graft. Desirably, the present invention has from about 800 to about 1,000 stitches per square centimeter (about 5,160 to about 6,500 stitches per square inch). Moreover, the knitted textile graft of the present invention has from about 14 to about 70 courses or wales per centimeter (about 35 to about 160 courses or wales per inch) to provide compliancy of the graft. The number of courses and wales per unit length may be the same or different. Desirably, the present invention has from about 14 to about 25 wales per centimeter (about 35 to about 64 wales per inch). More desirably, the present invention has from about 15.5 to about 17.5 wales per centimeter (about 39 to about 44 wales per inch). Furthermore, the present invention desirably has from about 31 to about 70 courses per centimeter (about 110 to about 160 courses per inch).

In one aspect of the present invention, the knitted textile graft is a knit structure of a single layer with at least a two-needle underlap. Because of the single layer construction the textile wall thickness is minimized to yield a low profile knitted textile graft. The textile wall thickness is from about 0.2 to about 0.4 millimeters. Desirably, the textile wall thickness is from about 0.27 to about 0.31 millimeters. Such thicknesses are measured with a one square inch pressed foot having a seven ounce weight, which results in measuring a one square inch section at a pressure of about 0.44 psi.

Furthermore, the knitted textile graft of the present invention has a burst strength from about 11 kg/cm$^2$ to about 16 kg/cm$^2$ (about 150 psi to about 220 psi). Desirably, the knitted textile graft of the present invention has a burst strength from about 13 kg/cm$^2$ to about 14 kg/cm$^2$ (about 170 psi to about 190 psi). The stretchability of the knitted textile graft is 50 to 220 percent at a one-kilogram of load. Knitted textile grafts with a stretchability of about 90 to 200 percent at one-kilogram load are also useful. Furthermore, knitted textile grafts with a stretchability of about 120 to 160 percent at one-kilogram load are also useful.

In a typical method of warp knitting the back yarn is fed from two inside beams, each beam being a spool holding a plurality of ends. Outside beams may be used in conjunction with the inside beams; the outside beams being used for feeding the front yarns. Each outside beam also has a plurality of ends. It should be noted, however, that the inside beams may be used for feeding the front yarn and the outside beams used for feeding the back yarn. Regardless of which beams are used, texturized flat yarn is generally used for both the front and back yarns. The minimum number of beams used in making the textile graft of the present invention is 2. A greater number of beams, however, may be found useful for specific applications. About eight to about sixteen guide beams or guide bars have been found to be particularly useful with the practice of the present invention.

Any type of textile product can be used as yarns for the knitted textile graft of the present invention. Of particular usefulness in forming the knitted fabric prosthesis of the present invention are synthetic materials such as synthetic polymers. Synthetic yarns suitable for use in the present invention include, but are not limited to, polyesters, including PET polyesters, polypropylenes, polyethylenes, polyurethanes and polytetrafluoroethylenes. The yarns may be of the monofilament, multifilament, spun type or combinations thereof. The yarns may also be flat, twisted or textured, and may have high, low or moderate shrinkage properties or combinations thereof.

The yarns used in forming the textile grafts of the present invention may be flat, twisted, textured or combinations thereof. Furthermore, the yarns may have high, low or moderate shrinkage properties or combination of different shrinkage properties. Additionally, the yarn type and yarn denier can be selected to meet specific properties desired for the prosthesis, such as porosity and flexibility. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used with the present invention may have a denier from about 20 to about 200, preferably from about 30 to about 100. Preferably, the yarns are polyester, such as polyethylene terephthalate (PET), and more preferably the yarns are one ply, 40 denier, 27 filament flat and texturized polyester yarns. Additionally, one ply, 50 denier, 48 filament flat polyester yarns are also useful.

After knitting the textile graft of the present invention is optionally cleaned or scoured in a basic solution of warm water, e.g., about 50° C. to about 65° C. (about 120° F. to about 150° F.), and detergent. The textile is then rinsed to remove any remaining detergent.

After the textile graft is optionally scoured, the graft is compacted or shrunk to reduce and control, in part, the porosity of the graft. Porosity of a knitted material is measured on the Wesolowski scale and by the procedure of Wesolowski. In the Wesolowski test, a fabric test piece is clamped flatwise and subjected to a pressure head of about 120 mm. of mercury. Readings are obtained which express the number of millimeters of water permeating per minute through each square centimeter of fabric. A zero reading represents absolute water impermeability and a value of about 20,000 represent approximate free flow of fluid.

The porosity of the textile graft 12 is often from about 7,000 to about 15,000 on the Wesolowski scale after being knitted on the double needle bar Raschel knitting machine. A more desirable porosity is from about 30 to about 5,000 on the Wesolowski scale and textile graft is compacted or shrunk in the wale direction to obtain the desired porosity. A solution of an organic component, such as hexafluoroisopropanol or trichloroacetic acid, and a halogenated aliphatic hydrocarbon, such as methylene chloride, is used to compact the textile graft by immersing it into the solution for up to 30 minutes at temperatures from about 15° C. to about 160° C. Other compacting solutions may suitably be used, such as those disclosed in U.S. Pat. Nos. 3,853,462 and 3,986,828, whose contents are incorporated by reference herein.

As noted above, preferably the tubular-knitted graft of the present invention is constructed of polyester which is capable of shrinking during a heat-set process. For instance, such grafts are typically flat-knitted in a tubular form. Due to the nature of the flat-knitting process, the tubular graft is generally flat in shape after knitting. Such grafts, however, when constructed of shrinkable polyester yarn, can be heat set on a mandrel to form a generally circular shape.

Such a heat-setting process is accomplished by first knitting the graft in a seamless tubular form out of a material capable of shrinking during a heat-setting or similar process. The graft may be preshrunk before it is placed on a mandrel. Preshrinking may be achieved by submitting the woven graft to moderate temperatures, such as from about 90° C. to about 205° C. (about 190° F. to about 400° F.). Usually the graft is placed in a medium for the preshrinking. Such a medium can include without limitation hot water, a chemical fluid, such as methylene chloride, or a gas, such as air or carbon dioxide. The graft of the present invention, however, may suitably be made without such a preshrinking of the yarns.

After the graft is knitted or alternatively knitted and preshrunk, the graft is placed on a mandrel, and heated in an oven at a temperature and time capable of causing the yarns of the graft to heat set to the shape and diameter of the mandrel. Preferably polyester yarns are used, and the heat setting is accomplished at time and temperatures appropriate for the material. For example, heat setting can be accomplished at about 90° C. to about 225° C. (about 190° F. to about 437° F.) for a period of about less than an hour. Temperatures in the range of about 130° C. to about 220° C. (about 260° F. to about 428° F.) are also useful. Desirably, temperatures from about 150° C. to about 215° C. (about 300° F. to about 419° F.) are also useful. Desirably, time periods from about 5 to about 30 minutes are useful. More desirably, with time periods from about 10 to about 20 minutes are useful. Other methods of heat setting known in the art may be employed. After such a heat setting process, the graft can be formed into a shape desired for implantation, having a generally circular inner lumen.

Figure 14:
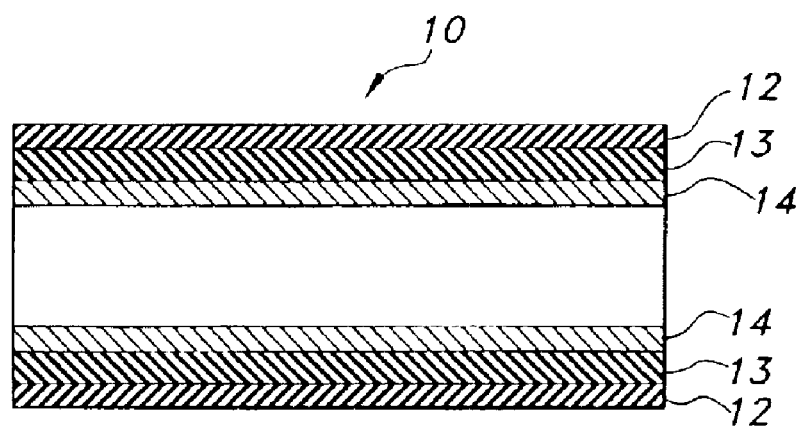
FIG. 14 is a cross-sectional view of the present invention which further includes a layer of e-PTFE disposed between the textile graft and the stent.

In another aspect of the present invention stent-graft 10 further includes a non-textile layer 13, as depicted in FIG. 14. The non-textile layer is circumferentially disposed between textile graft 12 and stent 14 and securably attached therebetween. One type of non-textile material particularly useful is polytetrafluoroethylene (PTFE). PTFE exhibits superior biocompatibility and low thrombogenicity, which makes it particularly useful as vascular graft material in the repair or replacement of blood vessels. Desirably the non-textile layer is a tubular structure manufactured from expanded polytetrafluoroethylene (ePTFE). The ePTFE material has a fibrous state which is defined by interspaced nodes interconnected by elongated fibrils. The space between the node surfaces that is spanned by the fibrils is defined as the internodal distance. When the term expanded is used to describe PTFE, it is intended to describe PTFE which has been stretched, in accordance with techniques which increase the internodal distance and concomitantly porosity. The stretching may be in uni-axially, bi-axially, or multi-axially. The nodes are spaced apart by the stretched fibrils in the direction of the expansion.

Desirably, the ePTFE material is a physically modified ePTFE tubular structure having enhanced axial elongation and radial expansion properties of up to 600 percent by linear dimension. The physically modified ePTFE tubular structure is able to be elongated or expanded and then returned to its original state without an elastic force existing therewithin. Such a physically modified ePTFE tubular structure is advantageously used in conjunction with wire-stent 22 of stent-graft 10.

Figure 16:
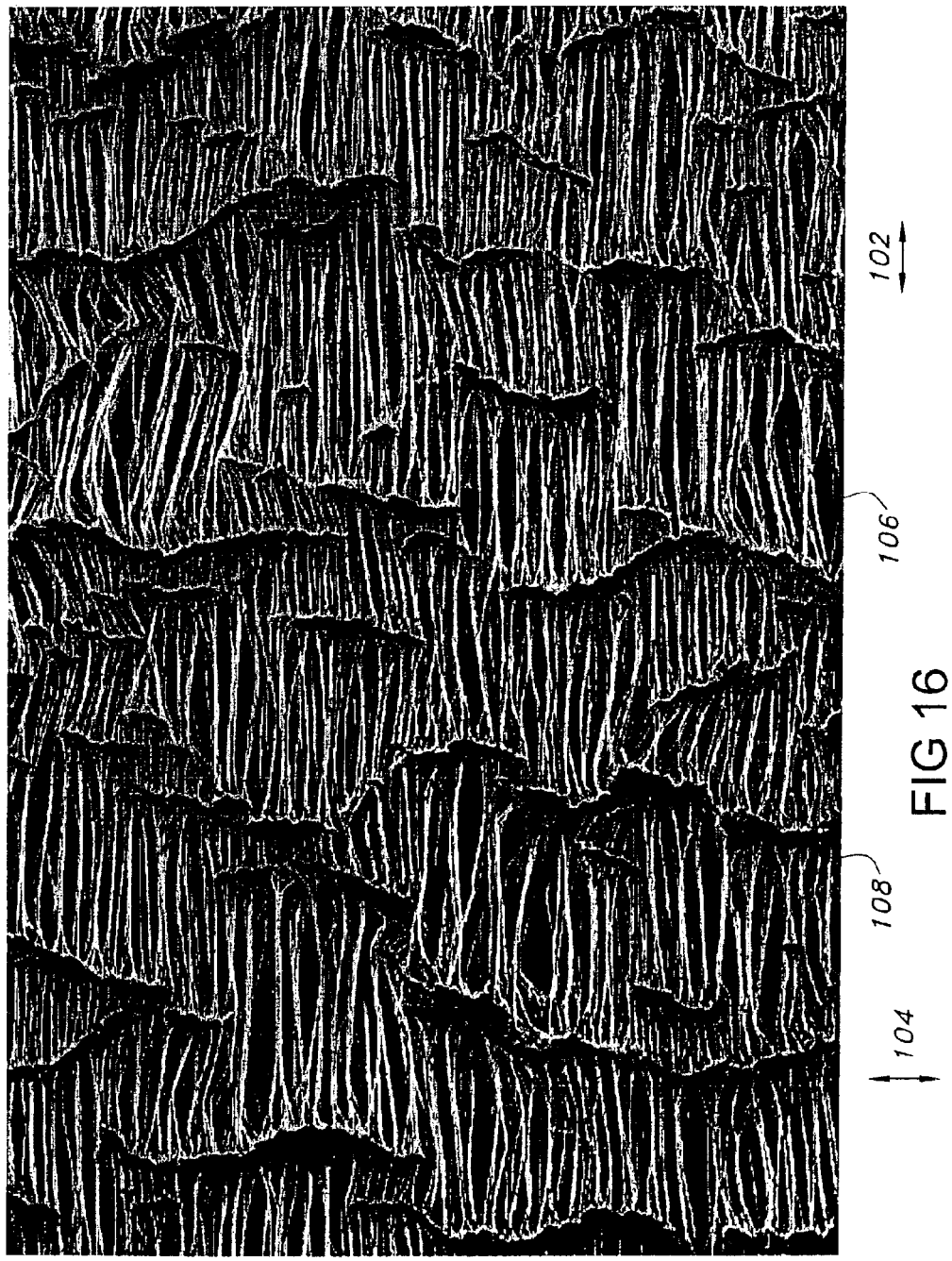
FIG. 16 is a photomicrograph showing a longitudinally expanded ePTFE structure.

FIG. 16 is a photomicrograph of a traditionally longitudinally expanded ePTFE tubular structure. The tube has been stretched in the longitudinal direction shown by directional arrow 102, leaving the nodes circumferentially oriented in circumferential direction shown by the directional arrow 104. The fibrils 106 are shown as being uniformly oriented in the longitudinal direction shown by directional arrow 102. Nodes 108 are shown and are uniformly oriented in circumferential direction 104.

Figure 17:
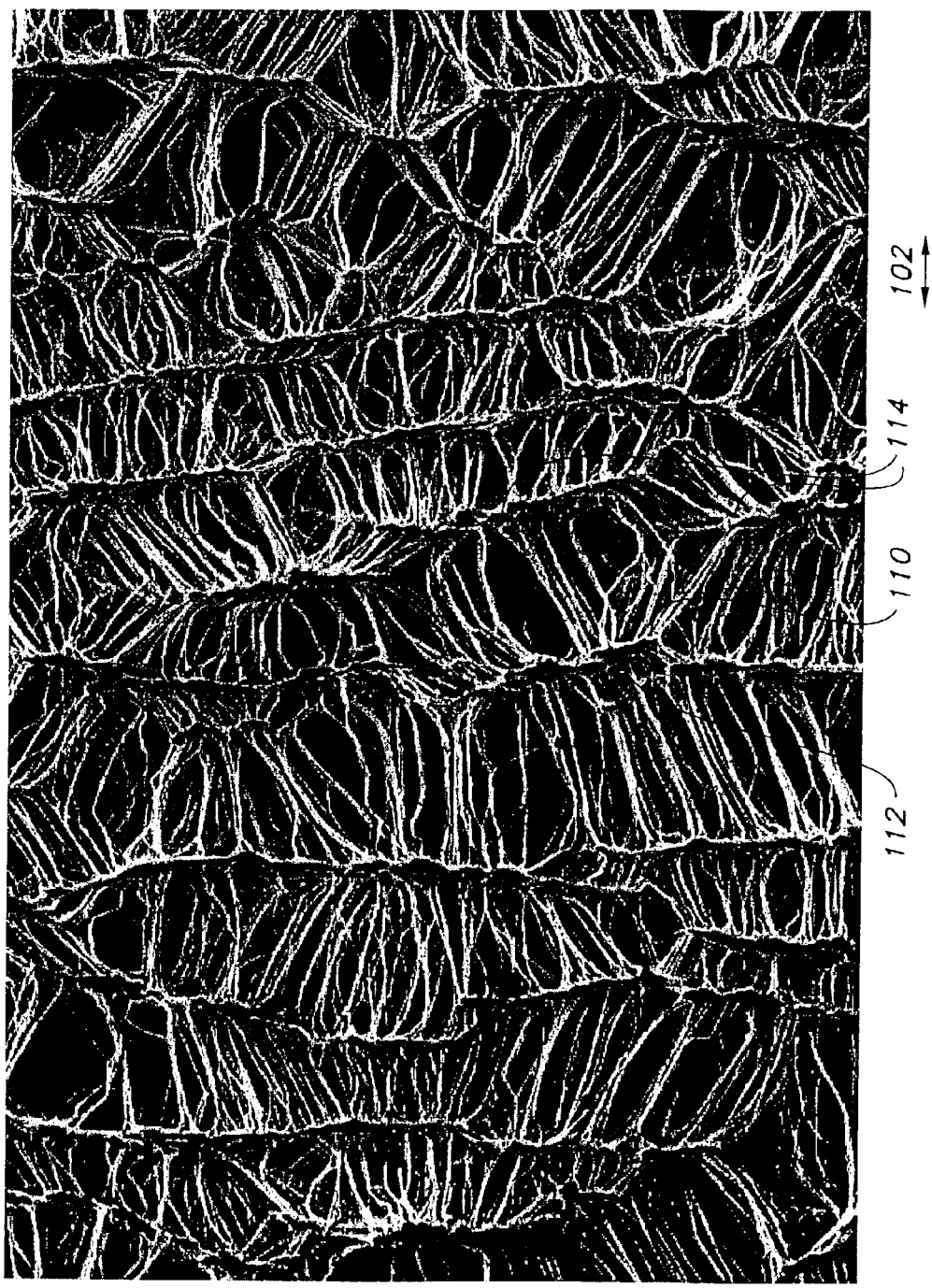
FIG. 17 is a photomicrograph of physically modified ePTFE structure having enhanced elongation properties as compared to the ePTFE structure of FIG. 16.
Figure 22:
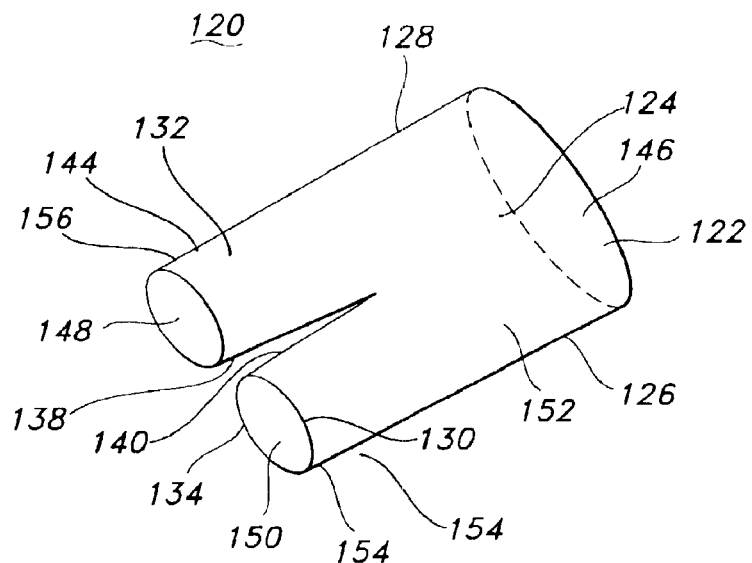
FIG. 22 is a perspective view of a bifurcated prosthesis according to the present invention.

FIG. 17 is a photomicrograph of the physically modified ePTFE tubular structure having circumferentially oriented nodes and longitudinally traversing fibrils. Nodes 110 are shown in the photomicrograph with a set of fibrils with first ends 112 and second ends 114 attached thereto. The fibrils with first ends 112 and second ends 114 are shown in a hingeably rotated position so that they are not substantially longitudinally oriented in the direction shown by directional arrow 102 as compared to the substantially longitudinally oriented parallel fibril structures 106 of FIG. 13. The term "hingeably rotated" and variants thereof refer to reorientation of previously uniformly oriented line segments by a change in position of one end of each line segment in relation to the other end of each segment, which remains fixed; i.e., the "hinge" about which the other end rotates. The reorientation takes place without a substantial change in dimension of the line segment. Additional details of the physically-modified ePTFE and methods for making the same can be found in commonly assigned application titled, "ePTFE Graft With Axial Elongation Properties", assigned U.S. application Ser. No. 09/898,415, filed on Jul. 3, 2001, published on Jan. 9, 2003 as U.S. Application Publication No. 2003/0009210 A1, the contents of which are incorporated by reference herein.

Figure 18:
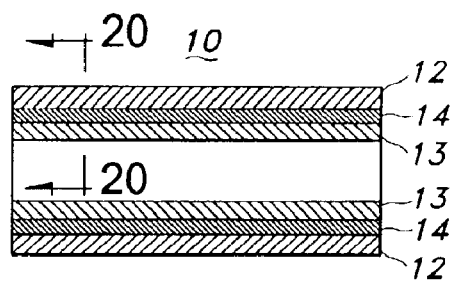
FIG. 18 is a cross-sectional view of another embodiment of the present invention which further includes a layer of e-PTFE disposed on the interior surfaces of the stent.
Figure 19:
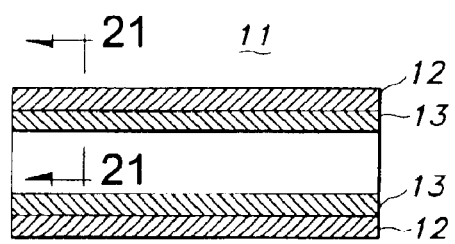
FIG. 19 is a cross-sectional view of a textile graft of the present invention having a layer of e-PTFE disposed on the interior surfaces of the graft.

In another aspect of the present invention stent-graft 10 may include a non-textile layer 13 disposed on interior portion of stent 14, as depicted in FIG. 18. In yet another aspect of the present invention, graft 11 may include a textile graft 12 and a non-textile layer 13, as depicted in FIG. 19. Desirably, non-textile layer 13 is circumferentially disposed on the interior portions of the textile graft 12.

Figure 21:
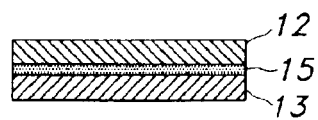
FIG. 21 is a partial cross-section view of the embodiment of FIG. 19 showing a bonding agent for securing the different elements thereat.

Non-textile layer 13 may be securably affixed to the textile graft 12, the stent 14, and combinations thereof. Desirably, a bonding agent 15 used for such securement, as depicted in FIGS. 20 and 21. The bonding agent 15 is used with the present invention is capable of adhesively securing the non-textile layer 13 to the textile graft 12 and/or to the stent 14 while also being capable of the 50 to 200 percent longitudinal expansion.

The bonding agent may include various biocompatible, elastomeric bonding agents such as urethanes, styrene/isobutylene/styrene block copolymers (SIBS), silicones, and combinations thereof. Other similar materials are contemplated. Desirably, the bonding agent may include polycarbonate urethanes sold under the trade name CORETHANE® This urethane is provided as an adhesive solution with preferably 7.5% Corethane, 2.5 W30, in dimethylacetamide (DMAc) solvent.

The composite textile graft and non-textile layer, i.e., graft 11, is desirably formed as follows. A thin non-textile, such as PTFE or ePFTE, tube is formed in a conventional forming process such as by tubular extrusion or by sheet extrusion where the sheet is formed into a tubular configuration. The non-textile tube is placed over a stainless steel mandrel (not shown) and the ends of the tube are secured. The non-textile tube is then spray coated with an adhesive solution, for example from about 1% to about 15% Corethane® urethane range, 2.5 W30 in DMAc. The coated non-textile tube is placed in an oven heated in a range from 18° C. to 150° C. for 5 minutes to overnight to dry off the solution. If desired, the spray coating and drying process can be repeated multiple times to add more adhesive to the non-textile tube. The coated non-textile tube is then covered with the textile graft to form a composite prosthesis. One or more layers of elastic tubing, preferably silicone, are then placed over this composite structure. This holds the composite structure together and assures that complete contact and adequate pressure is maintained for bonding purposes. The assembly of the composite graft within the elastic tubing is placed in an oven and heated in a range of 180° C. to 220° C. for approximately 5 to 30 minutes to bond the layers together. Additional details relating to useful bonding agents and their application to textile and non-textile surfaces may be found in U.S. application Ser. No. 10/167,676, filed Jun. 11, 2002, published on Jan. 23, 2003 as U.S. Patent Application Publication No. 2003/0017775, and in U.S. application Ser. No. 10/166,842, filed Jun. 11, 2002, published on Jul. 24, 2003 as U.S. Patent Application Publication No. 2003/0139806, both of which are entitled "Composite ePTFE/Textile Prosthesis" and both of which are incorporated herein by reference.

Moreover, the graft 11 may be crimped along the tubular surface thereof to impart longitudinal compliance, kink resistance and enhanced handling characteristics. The crimp may be provided by placing a coil of metal or plastic wire (not shown) around a stainless steel mandrel. The graft 11 is slid over the mandrel (not shown) and the coil wire. Another coil is wrapped around the assembly over the graft to fit between the spaces of the inner coil. The assembly is then heat set and results in the formation of the desired crimp pattern. It is further contemplated that other conventional crimping processes may also be used to impart a crimp to the graft 11.

Moreover, stent-graft 10 or graft 11 may be formed as an implantable prosthesis which is self-supporting and usable to maintain patency of a bodily vessel, such as in the coronary vasculature, esophagus, trachea, colon, biliary tract, urinary tract, prostate, and brain. Also, the textile portion 12 or the yarns forming textile portion 12 may be treated with any of the following therapeutic agents: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous or vascoactive mechanisms.

Figure 15:
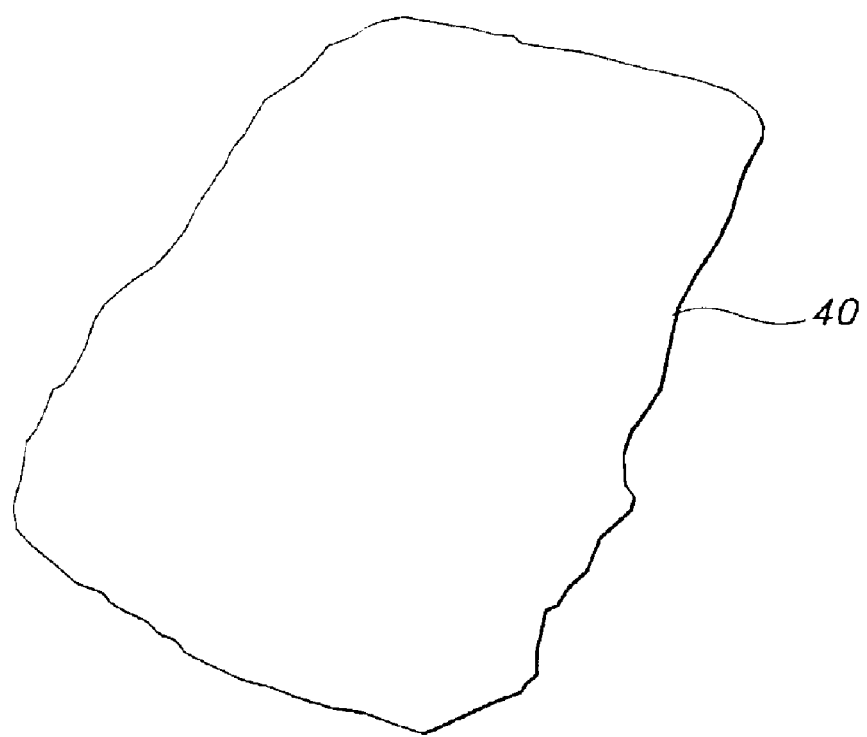
FIG. 15 is a partial perspective view of a knitted medical fabric of the present invention.

FIG. 15 is a partial perspective view of an implantable medical fabric 40, another aspect of the present invention. The medical fabric 40 is a warp-knitted textile fabric having at least a two needle underlap as described above. The medical fabric 40 has the features of the above-described textile graft 12, for instance, a high degree of stretchability. The medical fabric 40 of the present invention is useful in intraluminal applications, such as hernia repair.

The invention may be further understood with reference to the following non-limiting examples.

EXAMPLES

Example 1
Single Layer Stretch Knit Bifurcated Tubular Graft With a Two-Needle Underlap With Straight Tube (Body or Leg) knitting Details The following specifications are used to fabricate a solid knitted prosthesis of the present invention.

Yarn Type: Texturized polyethylene terephthalate (PET), 40 denier, 27 filaments.

Machine Type: 60 Gauge Karl Mayer Machine (30 needles per inch).

Number of Guide Bars: Sixteen

Guide bars 1–8, if threaded, were used for knitting the front of the graft and guide bars 9–16, if threaded, were used for the rear of the graft.

| 16 Guide Bar Layout: | | | | | | | | | | | | | | | |
|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 |
| G | G | 3-C-4 | | 5-C-6 | | 7-C-8 | | 9-C-10 | | 11-C-12 | | 13-C-14 | | G | G |

Notes:
G: Ground Bars
C: Nested Connect Bars

Guide Bar Threading Details: (Y-Threaded/n-Not Threaded)

72 Needle Bifurcated (BIF) Tube or Body

| Bar No. | Note: | ← | | | | (One Repeat Unit) | | | | | | → |
|---|---|---|---|---|---|---|---|---|---|---|---|---|
| #16 | not used | | n | N | n | n | n | n | N | n | n | n | n |
| #15 | | | n | Y | Y | Y | Y | n | n | Y | Y | Y | Y | n |
| #14 | R | Y | n | N | n | n | n | n | N | n | n | n | Y |
| #13 | CL | | n | N | n | n | n | Y | n | N | n | n | n | n |
| #12 | R | | n | N | n | n | n | n | N | n | n | Y | n |
| #11 | CR | | n | N | n | n | n | Y | N | n | n | n | n |
| #10 | not used | | n | N | n | n | n | n | N | n | n | n | n |
| #9 | not used | | n | N | n | n | n | n | N | n | n | n | n |
| #8 | not used | | n | N | n | n | n | n | N | n | n | n | n |
| #7 | not used | | n | N | n | n | n | n | N | n | n | n | n |
| #6 | CR | | n | N | n | n | n | Y | N | n | n | n | n |
| #5 | L | Y | N | n | n | n | n | n | N | n | n | n |
| #4 | CL | n | n | N | n | n | n | Y | n | N | n | n | n |
| #3 | L | Y | n | N | n | n | n | n | n | N | n | n | n |
| #2 | | n | n | Y | Y | Y | Y | n | n | Y | Y | Y | Y |
| #1 | not used | n | n | N | n | n | n | n | N | n | n | n |

Notes:
L: left body connect
R: right body connect
CL: left leg connect
CR: right leg connect
Bars 4 and 6 join front bar 2
Bars 11 and 13 join back bar 15
Total needles for BIF is 72 * 2 or 144 needles

42 Needle Straight Tube (ST) or Leg

| Bar No. | Note: | ← | | | (One Repeat Unit) | | | | → |
|---|---|---|---|---|---|---|---|---|---|
| #16 | not used | | n | n | n | n | n | n | n |
| #15 | | | n | Y | Y | Y | Y | Y | Y | n |
| #14 | R | Y | n | n | n | n | n | n | Y |
| #13 | CL | | n | n | n | n | n | n | n |
| #12 | R | | n | n | n | n | n | Y | n |
| #11 | CR | | n | n | n | n | n | n | n |
| #10 | not used | | n | n | n | n | n | n | n |
| #9 | not used | | n | n | n | n | n | n | n |
| #8 | not used | | n | n | n | n | n | n | n |
| #7 | not used | | n | n | n | n | n | n | n |
| #6 | CR | | n | n | n | n | n | n | n |
| #5 | L | Y | n | n | n | n | n | n | n |
| #4 | CL | n | n | n | n | n | n | n | n |
| #3 | L | Y | n | n | n | n | n | n | n |
| #2 | | n | n | Y | Y | Y | Y | Y | n |
| #1 | not used | n | n | n | n | n | n | n | n |

Notes:
L: left body connect
R: right body connect
CL: left leg connect
CR: right leg connect
Bars 4 and 6 join front bar 2
Bars 11 and 13 join back bar 15
Total needles for ST is (40 for body + 2 for connector) * 2 for total of 84 needles Guide Bar Chain Notation Details

Pattern Chains
Top Drum (Body): Channel 1

| Bar #1: | 0-0/0-0// | not used |
|---|---|---|
| Bar #2: | 0_2-0/4-4/4-6/2-2/ | 2-0/4-4/4-6/2-2_0// |
| Bar #3: | 0_4-2/4-4/2-2/2-0/ | 4-2/4-4/2-2/2-0// |
| Bar #4: | 0_2-0/4-4/4-6/2-2/ | 2-0/4-4/4-6/2-2_0// |
| Bar #5: | 0_2-0/2-2/4-4/4-2/ | 2-0/2-2/4-4/4-2_0// |
| Bar #6: | 0_2-0/4-4/4-6/2-2/ | 2-0/4-4/4-6/2-2_0// |
| Bar #7: | 0-0/0-0// | |
| Bar #8: | 0-0/0-0// | |
| Bar #9: | 0-0/0-0// | |
| Bar #10: | 0-0/0-0// | |
| Bar #11: | 0_2-2/4-6/2-2/2-0/ | 2-2/4-6/2-2/2-0// |
| Bar #12: | 0_2-2/2-4/0-2/0-0/ | 2-2/2-4/0-2/0-0// |
| Bar #13: | 0_2-2/4-6/2-2/2-0/ | 2-2/4-6/2-2/2-0// |
| Bar #14: | 0-0/0-2/2-4/2-2/ | 0-0/0-2/2-4/2-2_0// |
| Bar #15: | 0_2-2/4-6/2-2/2-0/ | 2-2/4-6/2-2/2-0// |
| Bar #16: | 0-0/0-0// | not used |

Pattern Chains
Bottom Drum (Legs): Channel 2

| Bar #1: | 0-0/0-0// | not used |
|---|---|---|
| Bar #2: | 0_2-0/4-4/4-6/2-2/ | 2-0/4-4/4-6/2-2_0// |
| Bar #3: | 0_4-2/4-4/2-2/2-0/ | 4-2/4-4/2-2/2-0// |
| Bar #4: | 0_2-2/2-4/4-6/2-2/ | 2-2/2-4/4-6/2-2_0// |
| Bar #5: | 0_2-0/2-2/4-4/4-2/ | 2-0/2-2/4-4/4-2_0// |
| Bar #6: | 0_2-0/2-2/4-4/4-2/ | 2-0/2-2/4-4/4-2_0// |
| Bar #7: | 0-0/0-0// | |
| Bar #8: | 0-0/0-0// | |
| Bar #9: | 0-0/0-0// | |
| Bar #10: | 0-0/0-0// | |
| Bar #11: | 0_4-2/4-4/2-2/2-0/ | 4-2/4-4/2-2/2-0// |
| Bar #12: | 0_2-2/2-4/0-2/0-0/ | 2-2/2-4/0-2/0-0// |
| Bar #13: | 0_2-2/4-6/2-4/2-2/ | 2-2/4-6/2-4/2-2_0// |
| Bar #14: | 0-0/0-2/2-4/2-2/ | 0-0/0-2/2-4/2-2_0// |

-continued

| | Pattern Chains Bottom Drum (Legs): Channel 2 | |
|---|---|---|
| Bar #15: | 0_2-2/4-6/2-2/2-0/ | 2-2/4-6/2-2/2-0// |
| Bar #16: | 0-0/0-0// | not used |

Graft Processing:

Subsequent to knitting the textile graft, the material is scoured in a basic solution of warm water (e.g., about 65° C. or about 150° F.) and cleaning detergent. It is then rinsed to remove the cleaning agents. The graft is then compacted with methylene chloride at elevated temperatures, for instance about 107° C. or about 224° F., for a short period of time, for instance, three minutes.

Next, the prosthesis is heat-set on stainless steel mandrels to achieve the final desired inside diameter. Typically, the outside diameter of the mandrel is typically twenty to forty percent oversized to impart, in part, high stretch and low dilation characteristics to the textile graft. Heat setting can take place in a convection oven at a temperature from about 120° C. (about 248° F.) to about 212° C. (about 414° F.) for about 5 to about 15 minutes. More desirably, the heat setting is at a temperature of about 180° C. (about 356° F.) for about 10 minutes.

As a result of the heat setting, the warp yarns are locked in the knitted geometry with a three-needle underlap to build in "spring like" properties that capable of longitudinal expansion. The heat set graft is capable of about 50 to 200 percent longitudinal expansion.

Example 2
Single Layer Knit Tubular Graft With a Three Needle Underlap

The following specifications are used to fabricate a solid knitted prosthesis of the present invention.

Yarn Type: Texturized polyethylene terephthalate (PET), 40 denier, 27 filaments.

Machine Type: 56 Gauge Kiddie Machine (28 needles per inch).

Number of Guide Bars: Eight

Guide Bar Threading Details: (y-Threaded/n-Not Threaded)

Guide Bar No. 8: y/y/y/y/y/y/y/y/n/n/n

Guide Bar No. 7: y/n/n/n/n/n/n/n/n/n

Guide Bar No. 6: n/n/n/n/n/n/n/n/n/y

Guide Bar No. 5: y/n/n/n/n/n/n/n/n/n

Guide Bar No. 4: n/n/n/n/n/n/n/n/y/n

Guide Bar No. 3: y/n/n/n/n/n/n/n/n/n

Guide Bar No. 2: y/n/n/n/n/n/n/n/n/n

Guide Bar No. 1: y/y/y/y/y/y/y/y/n/n

Guide Bar Position Details:

Guide Bar No. 1: 6-8-4-4/2-0-4-4/(repeat) Front Full Thread

Guide Bar No. 8: 4-4-2-0/4-4-6-8/(repeat) Back Full Thread

Guide Bar No. 2: 4-6-2-2/0-0-0-2/(repeat) Right Connect

Guide Bar No. 4: 2-4-0-0/2-2-2-4/(repeat) Right Connect

Guide Bar No. 6: 0-2-2-2/4-4-4-6/(repeat) Right Connect

Guide Bar No. 3: 2-2-2-0/6-4-4-4/(repeat) Left Connect

Guide Bar No. 5: 4-4-4-2/4-2-6-6/(repeat) Left Connect

Guide Bar No. 7: 6-6-6-4/2-0-4-4/(repeat) Left Connect

Graft Processing:

Subsequent to knitting the textile graft, the material is scoured in a basic solution of warm water (e.g., about 65° C. or about 150° F.) and cleaning detergent. It is then rinsed to remove the cleaning agents. The graft is then compacted with methylene chloride at elevated temperatures, for instance about 107° C. or about 224° F., for a short period of time, for instance, three minutes.

Next, the prosthesis is heat-set on stainless steel mandrels to achieve the final desired inside diameter. Typically, the outside diameter of the mandrel is typically twenty to forty percent oversized to impart, in part, high stretch and low dilation characteristics to the textile graft. Heat setting can take place in a convection oven at about 180° C. (about 356° F.) for about 10 minutes.

As a result of the heat setting, the warp yarns are locked in the knitted geometry with a three-needle underlap to build in "spring like" properties that capable of longitudinal expansion. The heat set graft is capable of about 50 to 200 percent longitudinal expansion.

Example 3
Single Layer Stretch Knit Straight Tubular Graft with a Two-Needle Underlap The following specifications were used to fabricate a super stretch knitted prosthesis of the present invention.

Yarn Type Used: Texturized polyethylene terephthalate (PET), 40 denier, 27 filaments.

Machine Used: 56 Gauge Kiddie Machine (28 needles per inch)

Guide Bars Used: 6

Guide Bar Threading Details: (y-threaded, n-not threaded):

| Guide Bar No. 6 | n | n | y | y | y | Y | y | y | y | y | n |
|---|---|---|---|---|---|---|---|---|---|---|---|
| Guide Bar No. 5 | n | y | n | n | n | N | n | n | n | n | n |
| Guide Bar No. 4 | n | n | n | n | n | N | n | n | n | n | y |
| Guide Bar No. 3 | n | n | n | n | n | N | n | n | n | y | n |
| Guide Bar No. 2 | y | n | n | n | n | N | n | n | n | n | n |
| Guide Bar No. 1 | n | n | y | y | y | Y | y | y | y | y | n |

Guide Bar Chain Notation Details:

| Guide Bar No. 1: | 2-0/4-4/4-6/2-2// repeat | Front full thread |
|---|---|---|
| Guide Bar No. 2: | 4-2/4-4/2-2/2-0// repeat | Left connector |
| Guide Bar No. 3: | 2-2/2-4/0-2/0-0// repeat | Right connector |
| Guide Bar No. 4: | 0-0/0-2/2-4/2-2// repeat | Right connector |
| Guide Bar No. 5: | 2-0/2-2/4-4/4-2// repeat | Left connector |
| Guide Bar No. 6: | 2-2/4-6/2-2/2-0// repeat | Back full thread |

Graft Processing:

Subsequent to knitting the textile graft, the material was scoured in a basic solution of warm water (e.g., about 65° C. or about 150° F.) and cleaning detergent. It was then rinsed to remove the cleaning agents. The graft was then compacted with methylene chloride at elevated temperatures, for instance about 107° C. or about 224° F., for a short period of time, for instance, three minutes.

Next, the prosthesis was heat-set on stainless steel mandrels to achieve the final desired inside diameter. Typically, the outside diameter of the mandrel was twenty to forty percent oversized to impart, in part, high stretch and low dilation characteristics to the textile graft. Heat setting was accomplished in a convection oven at about 180° C. (about 356° F.) for about 10 minutes.

As a result of the heat setting, the warp yarns were locked in the knitted geometry with a two-needle underlap to build in "spring like" properties that capable of longitudinal expansion. The heat set graft was capable of about 50 to 200 percent longitudinal expansion.

Example 4
Single Layer Stretch Knit Bifurcated Tubular Graft With a Two-Needle Underlap The following specifications were used to fabricate a bifurcated super stretch knitted prosthesis of the present invention.

Yarn Type Used: Texturized polyethylene terephthalate (PET), 40 denier, 27 filaments.

Machine Used: 56 Gauge Kiddie Machine (28 needles per inch)

Guide Bars Used: 10

Guide Bar Threading Details: (y-threaded, n-not threaded):

| | | | | | | | | | | | | |
|---|---|---|---|---|---|---|---|---|---|---|---|---|
| Guide Bar No. 10 | n | n | y | y | y | y | n | n | y | y | y | y | n |
| Guide Bar No. 9 | n | y | n | n | n | n | n | n | n | n | n | n | n |
| Guide Bar No. 8 | n | n | n | n | n | n | n | n | n | n | n | n | y |
| Guide Bar No. 7 | n | n | n | n | n | n | y | n | n | n | n | n | n |
| Guide Bar No. 6 | n | n | n | n | n | n | n | n | y | n | n | n | n |
| Guide Bar No. 5 | n | n | n | n | n | n | n | y | n | n | n | n | n |
| Guide Bar No. 4 | n | n | n | n | n | n | n | y | n | n | n | n | n |
| Guide Bar No. 3 | n | n | n | n | n | n | n | n | n | n | n | y | n |
| Guide Bar No. 2 | y | n | n | n | n | n | n | n | n | n | n | n | n |
| Guide Bar No. 1 | n | n | y | y | y | y | n | n | y | y | y | y | n |

Guide Bar Chain Notation Details:

| | | |
|---|---|---|
| Guide Bar No. 1: | 2-0/4-4/4-6/2-2// repeat | Front full thread |
| Guide Bar No. 2: | 4-2/4-4/2-2/2-0// repeat | Left connector |
| Guide Bar No. 3: | 2-2/2-4/0-2/0-0// repeat | Right connector |
| Guide Bar No. 4 Leg: | 4-4/4-2/2-0/2-2// repeat | Bifurcation connector |
| Guide Bar No. 4 Body: | 4-6/2-2/2-0/4-4// repeat | Join Bar No. 1 |
| Guide Bar No. 5 Leg: | 4-6/4-4/2-2/2-4// repeat | Bifurcation connector |
| Guide Bar No. 5 Body: | 4-6/2-2/2-0/4-4// repeat | Join Bar No. 1 |
| Guide Bar No. 6 Leg: | 2-4/2-2/4-4/4-6// repeat | Bifurcation connector |
| Guide Bar No. 6 Body: | 2-2/2-0/4-4/4-6// repeat | Join Bar No. 10 |
| Guide Bar No. 7 Leg: | 2-2/2-0/4-2/4-4// repeat | Bifurcation connector |
| Guide Bar No. 7 Body: | 2-2/2-0/4-4/4-6// repeat | Join Bar No. 10 |
| Guide Bar No. 8: | 0-0/0-2/2-4/2-2// repeat | Right connector |
| Guide Bar No. 9: | 2-0/2-2/4-4/4-2// repeat | Left connector |
| Guide Bar No. 10: | 2-2/4-6/2-2/2-0// repeat | Back full thread |

Graft Processing:

Subsequent to knitting the textile graft, the material was scoured in a basic solution of warm water (e.g., about 65° C. or about 150° F.) and cleaning detergent. It was then rinsed to remove the cleaning agents. The graft was then compacted with methylene chloride at elevated temperatures, for instance about 107° C. or about 224° F., for a short period of time, for instance, three minutes.

Next, the prosthesis was heat-set on stainless steel mandrels to achieve the final desired inside diameter. Typically, the outside diameter of the mandrel was twenty to forty percent oversized to impart, in part, high stretch and low dilation characteristics to the textile graft. Heat setting was accomplished in a convection oven at about 180° C. (about 356° F.) for about 10 minutes.

As a result of the heat setting, the warp yarns were locked in the knitted geometry with a two-needle underlap to build in "spring like" properties that capable of longitudinal expansion. The heat set graft was capable of about 50 to 200 percent longitudinal expansion.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An implantable tubular prosthesis capable of longitudinal expansion from a quiescent state to an elongated state comprising:

a radially contractible and longitudinally expandable tubular stent having a quiescent diameter and quiescent length capable of longitudinal expansion to the elongated state having an elongated length and a contracted diameter, wherein the elongated length is greater than the quiescent length and the contracted diameter is smaller than the quiescent diameter, and further wherein said stent is capable of resiliently returning from the elongated state to the quiescent state; and a knitted tubular graft circumferentially disposed and securably attached to said stent in the quiescent state, said graft having a single layer of yarns to define a single layered wall, said yarns being interlaced into stitches in a knit pattern capable of resilient longitudinal elongation and resilient radial contraction of said graft to the elongated state and having about at least 400 stitches per square centimeter and further having no more than about 1,200 stitches per square centimeter to provide compliancy in the quiescent state;

wherein said knit pattern is a warp knitted pattern of yarns forming a textile layer having an interior surface and an exterior surface, wherein exterior yarns comprise the exterior surface and form loops in the longitudinal direction of said prosthesis, and interior yarns comprise the interior surface and are diagonally shifted over two or more of the exterior yarns in an alternating pattern along a width of said prosthesis before engaging an exterior yarn.

2. The prosthesis of claim 1 wherein the elongated length is at least 50 percent by length greater than the quiescent length; and further wherein the elongated length is no more than about 220 percent by length greater than the quiescent length.

3. The prosthesis of claim 1 wherein said graft is substantially fluid-tight in the quiescent state.

4. The prosthesis of claim 1 wherein the interior yarns are diagonally shifted over three exterior yarns to define a three-needle underlap.

5. The prosthesis of claim 1 wherein the interior yarns are shifted over two exterior yarns to define a two-needle underlap.

6. The prosthesis of claim 1 wherein said diagonally shifted yarns inhibit radial expansion of said prosthesis to diameters greater than the quiescent diameter.

7. The prosthesis of claim 1 wherein said single layer of yarns form a graft wall having a thickness of about at least 0.2 millimeters; and
further wherein single layer of yarns form a graft wall having a thickness of no more than about 0.4 millimeters.

8. The prosthesis of claim 1 further including sutures for securably attaching said graft to said stent.

9. The prosthesis of claim 1 wherein said graft is mechanically attached to said stent.

10. The prosthesis of claim 1 wherein said graft is securably bonded to said stent.

11. The prosthesis of claim 1 wherein said stent has an exterior circumferential surface and further wherein said graft is circumferentially disposed to said exterior surface.

12. The prosthesis of claim 1 wherein said stent has an interior circumferential surface and further including a tubular layer of PTFE circumferentially disposed and securably attached to said interior surface of said stent.

13. The prosthesis of claim 12 further including a bonding agent disposed on an exterior surface of said tubular layer of PTFE for securably attaching said tubular layer of PTFE to said stent, to said graft or to said stent and said graft.

14. The prosthesis of claim 12 wherein said tubular layer of PTFE is a tubular layer of ePTFE.

15. The prosthesis of claim 14 wherein said tubular layer of ePTFE has circumferentially oriented nodes and longitudinally traversing fibrils.

16. The prosthesis of claim 1 wherein said stent is a wire-stent.

17. The prosthesis of claim 1 wherein said graft further includes opposed open ends to define a hollow tubular structure and further wherein one of said open ends of said graft is a bifurcated end having two hollow tubular structures.

18. The prosthesis of claim 16 wherein said stent further includes opposed open ends to define a hollow tubular structure and further wherein one of said open ends of said stent is a bifurcated end having two hollow tubular structures.

19. The prosthesis of claim 1 wherein said pattern has at least about 31 stitches per centimeter in the longitudinal direction of said prosthesis; and
further wherein said pattern has no more than about 70 stitches per centimeter in the longitudinal direction of said prosthesis.

20. The prosthesis of claim 1 wherein said pattern has at least about 14 stitches per centimeter along the width of said prosthesis; and
further wherein said pattern has no more than about 25 stitches per centimeter along the width of said prosthesis.

21. An implantable tubular prosthesis capable of longitudinal expansion from a quiescent state to an elongated state comprising:
a radially contractible and longitudinally expandable tubular stent having an interior surface and an exterior surface and further having a quiescent diameter and quiescent length capable of longitudinal expansion to the elongated state having an elongated length and a contracted diameter, wherein the elongated length is greater than the quiescent length and the contracted diameter is smaller than the quiescent diameter, and further wherein said stent is capable of resiliently returning from the elongated state to the quiescent state;
a non-textile tubular member circumferentially disposed and securably attached to said interior surface of said stent;
a knitted tubular graft circumferentially disposed to said exterior surface of said stent and securably attached to said non-textile tubular member, said graft having a single layer of yarns to define a single layered graft wall, said yarns being interlaced into stitches in a knit pattern capable of resilient longitudinal elongation and resilient radial contraction of said graft to the elongated state and having greater than about 350 stitches per square centimeter to provide compliancy in the quiescent state;
wherein said knit pattern is a warp knitted pattern of yarns forming a textile layer having an interior surface and an exterior surface, wherein exterior yarns comprise the exterior surface and form loops in the longitudinal direction of said prosthesis, and interior yarns comprise the interior surface and are diagonally shifted over two or more of the exterior yarns in an alternating pattern along a width of said prosthesis before engaging an exterior yarn; and further wherein said interior yarns inhibit radial expansion of said exterior yarns to inhibit dilation of said prosthesis.

22. The prosthesis of claim 21 further including a bonding agent disposed on an exterior surface of said non-textile tubular tube for securably attaching said non-textile tubular member to said stent, to said graft or to said stent and said knitted tubular graft.

23. The prosthesis of claim 22 wherein said bonding agent is a polycarbonate urethane adhesive.

24. The prosthesis of claim 21 wherein said non-textile tubular member is a tubular layer of PTFE.

25. The prosthesis of claim 21 wherein said non-textile tubular member is a tubular layer of ePTFE.

26. The prosthesis of claim 25 wherein said tubular layer of ePTFE has circumferentially oriented nodes and longitudinally traversing fibrils.

27. The prosthesis of claim 21 wherein said stent is a wire-stent.

28. The prosthesis of claim 21 further including sutures for securably attaching said graft to said stent.

29. The prosthesis of claim 21 wherein said graft is mechanically attached to said stent.

30. The prosthesis of claim 21 wherein said graft is securably bonded to said stent.

31. An implantable tubular graft comprising:
a knitted tubular graft having a single layer of yarns to define a single layered wall having an interior surface and an exterior surface, said yarns being interlaced into stitches in a knit pattern capable of resilient longitudinal elongation and resilient radial contraction of said graft to the elongated state and having greater than about 350 stitches per square centimeter to provide compliancy in the quiescent state; and
a non-textile tubular member circumferentially disposed and securably attached to said interior surface of said knitted tubular graft;
wherein said knit pattern is a warp knitted pattern of yarns forming a textile layer having an interior surface and an exterior surface, wherein exterior yarns comprise the exterior surface and form loops in the longitudinal direction of said graft, and interior yarns comprise the interior surface and are diagonally shifted over two or more of the exterior yarns in an alternating pattern along a width of said graft before engaging an the exterior yarn.

32. The graft of claim 31 further including a bonding agent disposed on an exterior surface of said non-textile tubular member for securably attaching said non-textile tubular member to said graft.

33. The graft of claim 31 wherein said interior yarns are diagonally shifted over from two to three the exterior yarns.

34. The graft of claim 31 wherein said single layer of yarns form a graft wall having a thickness of at least about 0.3 millimeters; and further wherein said single layer of yarns form a graft wall having a thickness of no more than about 0.4 millimeters.

35. The graft of claim 31 wherein the longitudinal expansion is at least about 50 percent by length of the length in the quiescent state; and further wherein the longitudinal expansion is no more than about 200 percent by length of the length in the quiescent state.

36. The graft of claim 31 wherein said graft has a substantially fluid-tight quiescent state.

37. The graft of claim 31 wherein said yarns are selected from the group consisting of monofilament yarns, multifilament yearns, spun type yarns, flat yarns, twisted yarns, textured yarns, and combinations thereof.

38. The graft of claim 31 wherein said yarns are selected from the group of materials selected from polyesters, polypropylenes, polyethylenes, polyurethanes, polytetrafluoroethylenes or combinations thereof.

39. The graft of claim 38 wherein said polyesters include polyethylene terephthalate polyesters.

40. The graft of claim 31 wherein said yarns are polyethylene terephthalate polyester textured yarns having a denier of at least about 30; and further wherein said polyethylene terephthalate polyester textured yarns have a denier of less than about 100.

41. The graft of claim 31 wherein said pattern has at least about 31 stitches per centimeter in the longitudinal direction of the graft; and further wherein said pattern has no more than about 70 stitches per centimeter in the longitudinal direction of the graft.

42. The graft of claim 31 wherein said pattern has at least about 14 stitches per centimeter along the width of the graft; and further wherein said pattern has no more than about 25 stitches per centimeter along the width of the graft.

* * * * *

UNITED STATES PATENT AND TRADEMARK OFFICE
CERTIFICATE OF CORRECTION

PATENT NO. : 6,939,372 B2
DATED : September 6, 2005
INVENTOR(S) : Dong, J.

It is certified that error appears in the above-identified patent and that said Letters Patent is hereby corrected as shown below:

Column 2,
Lines 17-18, should read -- ..and must subsequently be unfolded.. --.
Lines 54-55, should read -- ...result in complicated stent-graft... --.

Column 4,
Line 29, should read -- ...before engaging the exterior yarn. --.

Column 8,
Line 24, should read -- In Fig. 11A, needle positions... --.

Column 9,
Line 15, should read -- Figure 11B is an illustration... --.
Line 23, should read -- ...interloopng with yarn 36d. --.
Line 24, should read -- ...in the opposite course direction... --.

Column 21,
Line 29, should read -- ...properties that are capable of longitudinal... --.

Column 22,
Line 17, should read -- ...properties that are capable of longitudinal... --.

Column 23,
Line 6, should read -- ...properties that are capable of longitudinal... --.

Column 24,
Line 12, should read -- ...properties that are capable of longitudinal... --.

UNITED STATES PATENT AND TRADEMARK OFFICE
CERTIFICATE OF CORRECTION

PATENT NO. : 6,939,372 B2
DATED : September 6, 2005
INVENTOR(S) : Dong, J.

It is certified that error appears in the above-identified patent and that said Letters Patent is hereby corrected as shown below:

Column 27,
Line 2, should read -- ...two to three exterior yarns. --.

Signed and Sealed this

Twenty-eighth Day of March, 2006

JON W. DUDAS
*Director of the United States Patent and Trademark Office*